(12) United States Patent
Ahn et al.

(10) Patent No.: US 9,610,310 B2
(45) Date of Patent: Apr. 4, 2017

(54) PHARMACEUTICAL COMPOSITION FOR PREVENTING OR TREATING INFLAMMATORY DISEASES OR ASTHMA, CONTAINING LAGERSTROEMIA OVALIFOLIA EXTRACT OR FRACTION THEREOF AS ACTIVE INGREDIENT

(71) Applicant: Korea Research Institute of Bioscience and Biotechnology, Daejeon (KR)

(72) Inventors: Kyung Seop Ahn, Daejeon (KR); Sei Ryang Oh, Daejeon (KR); Ok Kyoung Kwon, Daejeon (KR); Fifit Juniarti, Jakarta (ID); Rifatul Widjhati, Jakarta (ID); Ji Won Park, Daejeon (KR); Jin Hyub Paik, Daejeon (KR); Joong Ku Lee, Daejeon (KR); Hyeong Kyu Lee, Daejeon (KR); Sang Ho Choi, Daejeon (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 0 days.

(21) Appl. No.: 14/369,595

(22) PCT Filed: Dec. 28, 2012

(86) PCT No.: PCT/KR2012/011777
§ 371 (c)(1),
(2) Date: Jun. 27, 2014

(87) PCT Pub. No.: WO2013/100718
PCT Pub. Date: Jul. 4, 2013

(65) Prior Publication Data
US 2014/0370126 A1  Dec. 18, 2014

(30) Foreign Application Priority Data
Dec. 30, 2011 (KR) ........................ 10-2011-0147705

(51) Int. Cl.
*A61K 36/185* (2006.01)

(52) U.S. Cl.
CPC .................................. *A61K 36/185* (2013.01)

(58) Field of Classification Search
None
See application file for complete search history.

(56) References Cited

FOREIGN PATENT DOCUMENTS

| JP | 05-310587 | | 11/1993 |
|---|---|---|---|
| JP | 07126143 | A | 5/1995 |
| JP | 07-228539 | A | 8/1995 |
| JP | 10-291935 | A | 11/1998 |
| JP | 2005139070 | A | 6/2005 |
| KR | 10-2011-0050938 | | 5/2011 |
| KR | 1020110050938 | A | 5/2011 |
| KR | 10-2011-0056278 | | 6/2011 |
| WO | WO-2011-158247 | | 12/2011 |

OTHER PUBLICATIONS 2008 http://web.archive.org/web/20080616123525/http://my.clevelandclinic.org/heart/disorders/valve/sbe.aspx.*
Mazumder, Avijit PhD. Thesis (2005).
Judy et al "Antidiabetic Activity of a Standardized Extract (Glucosol™) from *Lagerstroemia speciosa* Leaves in Type II Diabetics a Dose-Dependence Study" Journal of Ethnopharmacology vol. 37, pp. 115-117. 2003.
Priya et al "Free Radical Scavenging and Anti-Inflammatory Properties of *Lagerstroemia speciosa* (L)" Inflammopharmacology vol. 16, pp. 182-187. 2008.
Yang et al "Anti-Inflammatory Effects of Ethanolic Extract from *Lagerstroemia Indica* on Airway Inflammation in Mice" Journal of Ethnopharmacology vol. 136, pp. 422-427. 2011.
Kou, et al., "The Emerging Multifaceted Roles of Nitic Oxide", Annals of Surgery, vol. 221, No. 3, 1995.
Lawrence, et al., "Possible new role for NF-kB in the resolution of inflammation", Nature Medicine, vol. 7, No. 12, Dec. 2001.
Elias, et al., "New insights into the pathogenesis of asthma", Journal of Clinical Investication, vol. 111, No. 3, Feb. 2003.
Maggi, "The TH1/TH2 paradigm in allergy", Immunotechnology, vol. 3, 1998.
Barnes, et al., "Inflammatory Mediators of Asthma: An Update", Pharmacological Reviews Col. 50, No. 4, 1998.
Warshamana, et al., "Dexamethasone activates expression of the PDGF-α receptor and induces lung fibroblast proliferation", American Physiological Society, 1998.
PK, et al., "Effects of treatment on airway inflammation and thickening of basement membrane reticular collagen in asthma. A quantitative light and electron microscopic study", Am Rev Respir Dis, vol. 145, No. 4, Pt. 1, 1992.
Garcia, et al., "Montelukast, Compared with Fluticasone, for Control of Asthma Among 6-to-14-Year-Old Patients with Mild Asthma: The MOSAIC Study", Official Journal of the American Academy of Pediatrics, 2005.

* cited by examiner

*Primary Examiner* — Terry A McKelvey
*Assistant Examiner* — Catheryne Chen
(74) *Attorney, Agent, or Firm* — Cesari and McKenna LLP

(57) ABSTRACT

The present invention relates to a pharmaceutical composition for preventing or treating inflammatory diseases or asthma comprising a *Lagerstroemia ovalifolia* extract or a fraction thereof as an active ingredient, and a health functional food and a feed additive for preventing or improving inflammatory diseases or asthma comprising the extract or the fraction as an active ingredient.

6 Claims, 11 Drawing Sheets

PHARMACEUTICAL COMPOSITION FOR PREVENTING OR TREATING INFLAMMATORY DISEASES OR ASTHMA, CONTAINING LAGERSTROEMIA OVALIFOLIA EXTRACT OR FRACTION THEREOF AS ACTIVE INGREDIENT

CROSS REFERENCE TO RELATED APPLICATIONS

This application is the National Stage of International Application No. PCT/KR2012/011777, filed on Dec. 28, 2012, which claims the benefit of Korean Patent Application No. 10-2011-0147705 filed on Dec. 30, 2011. The contents of both applications are hereby incorporated by reference in their entirety.

TECHNICAL FIELD

The present invention relates to a pharmaceutical composition for preventing or treating inflammatory diseases or asthma comprising a *Lagerstroemia ovalifolia* extract or a fraction thereof as an active ingredient, and to a health functional food and feed additive for preventing or ameliorating inflammatory disease or asthma comprising the extract or fraction as an active ingredient.

BACKGROUND ART

An inflammatory response occurs when a tissue (cell) is injured or infected by foreign infectious agents (bacteria, fungi, viruses, or various allergens). It involves a series of complex physiological responses, including enzymatic activation, secretion of inflammation mediators, infiltration of body fluid, cell migration, and tissue damage, which are associated with various inflammation mediators and immunocytes in local blood vessels and body fluid. It also involves external symptoms such as erythema, edema, pyrexia and pain. Specifically, when external bacteria infiltrate a specific tissue and proliferate therein, leukocytes in the body recognize and actively attack the proliferated external bacteria. Dead leukocytes caused during this process are accumulated in the tissue infected by the bacteria while cells of the infiltrated bacteria killed by leukocytes are lysed in the tissue, resulting in formation of abscesses.

In the case of normal persons, inflammatory responses act to remove foreign infectious agents and regenerate injured tissue to restore the functions of the body. However, when an antigen is not removed or inflammatory responses occur excessively or continuously due to intrinsic substances, inflammatory responses cause life threatening diseases, including acute inflammation, joint diseases such as rheumatoid arthritis, skin diseases such as psoriasis, and allergic inflammatory diseases such as bronchial asthma, and also act as obstacles to treatment processes such as blood transfusion, drug administration and organ transplantation.

With recent developments in molecular biology, understanding of inflammatory diseases at the level of cytokine molecules has been attempted, and factors that influence such diseases have been identified one by one. Among such factors, nitric oxide (NO), an inflammatory mediator, acts to maintain homeostasis by performing a defensive function that damages pathogenic DNA (Kou and Schroder, Annuals of Surgery 221, 220-235, 1995).

NO is produced from L-arginine by three major nitric oxide synthase (NOS) isomers: nNOS (neuronal NOS), eNOS (endothelial NOS), and iNOS (inducible NOS). nNOS and eNOS are regulated by $Ca^{2+}$/calmodulin, but iNOS is regulated at the transcriptional level by inflammatory stimuli such as interleukin, interferon and LPS. As is known in the art, NO produced in small amounts by nNOS or eNOS plays a role in normal physiological functions such as vasodilation, neurotransmission, and cell lysis against pathogens, but NO produced in excessive amounts by iNOS in macrophages is involved in a variety of pathophysiological processes including inflammation and cancer and reacts with superoxide to form peroxynitrite, which acts as a potent oxidant that damages cells and activates NF-B in macrophages activated by inflammatory stimuli, resulting in inflammatory responses and chronic diseases such as cancer and arteriosclerosis (Lawrence et al., Nat Med., 7:1291-1297, 2001).

Prostaglandin $E_2$ ($PGE_2$) and leukotriene are also inflammatory mediators that are produced from arachidonic acid. Particularly, $PGE_2$ is produced by cyclooxygenase-2 (COX-2) enzyme and is produced mainly in macrophages and monocytes.

Asthma is a chronic inflammatory disease that is caused in the airway or lung by complex immune responses. It shows clinical symptoms, including wheezing caused by constriction of the airway due to various stimuli, difficulty in breading, and coughing, and can get better alleviated naturally or by treatment. Most asthmas are allergic diseases that frequently occur today, and show, in addition to chronic airway inflammation, airway obstruction symptoms caused by formation of allergen-specific immunoglobulin E (IgE) antibody, excessive secretion of airway mucus, or airway hypersensitivity.

Asthmas can be classified into extrinsic asthma and intrinsic asthma according to their cause. The term "extrinsic asthma" refers to asthma whose symptoms appear upon exposure to a causative antigen. It usually shows a positive response to a skin test or bronchial provocation test against the causative antigen and generally occurs in a young age group. House dust and mites are the most frequent causative antigens, and in addition, pollens, animal epithelium, molds also act as the causative antigens. Intrinsic asthma is caused or becomes worse by upper airway infection, exercise, emotional unrest, cold climate and humidity change and can be frequently seen in an adult group. In addition, there are drug-induced asthma, exercise-induced asthma, and occupational asthma.

Considering the rapid increase in allergic diseases in the past 30 years, it has been strongly suggested that asthma is caused mainly by extrinsic factors rather than intrinsic factors such as genetic factors. Among such extrinsic factors, the change in the immune system of the body by an external environment is most predominant. Particularly, asthma is recognized as a chronic inflammatory disease that is caused by the proliferation, differentiation and activation of inflammatory cells by interleukin-4, interleukin-5 or interleukin-13, which is produced in TH2 (T helper 2) type immune cells by allergens, and the migration and infiltration of the inflammatory cells into the airway and tissue surrounding the airway (Elias J A, et al., J. Clin. Invest., 111, pp 291-297, 2003). In this case, inflammatory cells, including activated eosinophils, mast cells and alveolar macrophages, secrete various inflammatory mediators (cysteine leukotrienes, prostaglandins, etc.) while strong constriction of bronchi plays an important role in the process (Maggi E., Immunotechnology, 3, pp 233-244, 1998; Pawankar R., Curr. Opin. Allergy Clin. Immunol., 1, pp 3-6, 2001; Barnes P J, et al., Pharmacol Rev., 50, pp 515-596, 1998).

Until now, a variety of therapeutic agents have been commonly used, but a considerable number of therapeutic agents should be used with care, because they can cause side effects. At present, inhaled corticosteroid formulations are most frequently used as therapeutic agents and show excellent effects. However, it is known that, when these formulations are used for a long period of time, they cause adrenal gland inhibition, a decrease in bone density, growth disorders, complications of eyes and skin, in proportion to the dose and time of use thereof. In addition, it was reported that the corticosteroid formulations can increase the synthesis of collagen (Warshmana G S, et al. Dexamethasone activates expression of the PDGF-alpha receptor and induces lung fibroblast proliferation. Am J Physiol 274, 499-507, 1998). For these reasons, even though the treatment of chronic asthma patients with corticosteroids has been performed for several years, asthma patients in which airway hypersensitivity was suppressed to a normal state were rare. Moreover, it is known that long-term administration of a beta-2 agonist does not suppress the reconstitution of the airway (Jeffery P K, et al. Effects of treatment on airway inflammation and thickening of basement membrane reticular collagen in asthma. A quantitative light and electron microscopic study. Am Rev Respir Dis 145: 890-0, 1992). In addition, it was reported that long-lasting beta-2 agonists such as salmeterol and formeterol can cause the death of asthma patients, even though they can prevent asthma attacks. Although various side effects as described above have been reported, these agents have been continuously prescribed under the judgment that the effect of alleviating asthma symptoms is greater than the risk of side effects. However, the results of measuring the growth rate of child asthma patients indicated that the growth rate of child asthma patients administered with an oral leukotriene antagonist (montelukast) was higher by up to 1 cm per year than that of child asthma patients administered with an inhaled corticosteroid formulation (Garcia Garcia M L, et al. Montelukast, compared with fluticasone, for control of asthma among 6- to 14-year old patients with mild asthma: the MOSAIC study. Pediatrics 116 (2): 360-9, 2005). When asthma in the growth phase is not controlled, the growth of not only the lungs, but also other parts of the body, can be inhibited. For this reason, it is essential for growth to maintain normal lung functions by continuous treatment. However, because it is particularly important to use a safe drug for continuous treatment and sufficiently control inflammation of the airway, side effects together with asthma alleviating effects should be carefully considered in the selection of therapeutic agents.

Thus, there has been a need for the development of drugs which have excellent immunotherapeutic and anti-inflammatory effects and cause little or no side effects, and thus can be safely used for a long period of time. For this reason, studies on the development of materials from natural resources through verifications of the effects thereof have been activated.

Meanwhile, the genus *Lagerstroemia* includes about 50 kinds of plants. Among them, *Lagerstroemia indica* L. is known to have the effects of stopping bleeding and removing tumors, and is known to be effective against metrorrhagia, leukorrhea with reddish discharge, traumatic bleeding, enteritis, diarrhea and the like. An extract of *Lagerstroemia indica* L. and the active ingredient thereof are known to have anti-allergic effects (Korean Patent Laid-Open Publication No. 10-2011-0050938). In addition, *Lagerstroemia speciosa* is effective against diabetes and obesity, and a *Lagerstroemia speciosa* leaf extract is known to have an antioxidant effect (Japanese Patent Laid-Open Publication No. 1998- 291935). However, the anti-inflammatory activity or anti-asthma activity of *Lagerstroemia ovalifolia* among plants belonging to the genus *Lagerstroemia* has not yet been known.

DISCLOSURE

Technical Problem

The present inventors have conducted studies to develop an agent for preventing and treating inflammatory diseases, which is derived from natural materials, is not toxic and causes no side effects, and as a result, have found that a *Lagerstroemia ovalifolia* extract and a fraction thereof show no toxicity and can significantly inhibit the production of the inflammatory mediators NO, iNOS, PEG2, COX-2, IL-6 and IL-1β. In addition, the present inventors have found that the *Lagerstroemia ovalifolia* extract and a fraction thereof have the effects of alleviating airway hypersensitivity, inhibiting the infiltration of inflammatory cells into the bronchus, reducing the levels of cytokines in bronchoalveolar lavage fluid, inhibiting the secretion of blood immunoglobulin, and inhibiting the mucous secretion of globlet cells in ovalbumin-induced asthma mouse models, suggesting that they are useful against inflammatory diseases and asthma, thereby completing the present invention.

Technical Solution

It is an object of the present invention to provide a pharmaceutical composition for preventing or treating inflammatory diseases or asthma comprising a *Lagerstroemia ovalifolia* extract or a fraction thereof as an active ingredient.

Another object of the present invention is to provide the use of a *Lagerstroemia ovalifolia* extract or a fraction thereof for preventing or treating inflammatory diseases or asthma.

Still another object of the present invention is to provide a method for preventing or treating inflammatory diseases or asthma, the method comprising administering to a subject in need thereof a pharmaceutical composition comprising a *Lagerstroemia ovalifolia* extract or a fraction thereof as an active ingredient.

Still another object of the present invention is to provide a health functional food for preventing or ameliorating inflammatory diseases or asthma comprising a *Lagerstroemia ovalifolia* extract or a fraction thereof as an active ingredient.

Still another object of the present invention is to provide a feed additive for preventing or ameliorating inflammatory diseases or asthma comprising a *Lagerstroemia ovalifolia* extract or a fraction thereof as an active ingredient.

Advantageous Effects

A *Lagerstroemia ovalifolia* extract according to the present invention and a fraction thereof show no toxicity and have an excellent activity of inhibiting the production of the inflammatory mediators NO, iNOS, $PEG_2$, COX-2, IL-6 and IL-1β. In addition, the *Lagerstroemia ovalifolia* extract and a fraction thereof showed excellent effects of alleviating airway hypersensitivity, inhibiting the infiltration of inflammatory cells into the bronchus, reducing the levels of cytokines in bronchoalveolar lavage fluid, inhibiting the secretion of blood immunoglobulin, and inhibiting the mucous secretion of globlet cells in ovalbumin-induced asthma mouse models, suggesting that they can be effectively used as agents for preventing and treating inflammatory diseases or asthma.

DESCRIPTION OF DRAWINGS

FIG. 3a) is a graphic diagram showing NO production, in which ($) indicates P<0.05 versus negative control, (*) indicates P<0.005 versus positive control, and (#) indicates P<0.0005 versus positive control. First bar from the left: negative control group administered with 0.15% DMSO alone; second bar from the left: positive control group treated with 0.5 μg/ml of LPS to induce inflammation; the remaining bars: groups treated with various concentrations of a *Lagerstroemia ovalifolia* extract, and then treated with LPS to induce inflammation;

FIGS. 3b) and 3c) show the results of nucleic acid amplification analysis and Western blotting analysis, respectively, performed after treatment with various concentrations of a *Lagerstroemia ovalifolia* extract together with negative and positive control groups. Negative control group: group administered with 0.15% DMSO alone (first from the left); and positive control group: group treated with 0.5 μg/ml of LPS to induce inflammation (second from the left).

FIG. 4a) is a graphic diagram showing the production of $PGE_2$, in which ($) indicates P<0.05 versus negative control, and (*) indicates P<0.005 versus positive control. First bar from the left: negative control group treated with 0.15% DMSO alone; second bar from the left: positive control group treated with 0.5 μg/ml of LPS to induce inflammation; and the remaining bars: test groups treated with various concentrations of a *Lagerstroemia ovalifolia* extract, and then treated with LPS to induce inflammation.

FIGS. 4b) and 4c) show the results of nucleic acid amplification analysis and Western blotting analysis, respectively, performed after treatment with various concentrations of a *Lagerstroemia ovalifolia* extract together with negative and positive control groups. Negative control; group: group administered with 0.15% DMSO alone (first from the left); and positive control group: group treated with 0.5 μg/ml of LPS to induce inflammation (second from the left).

BEST MODE

Figure 1:
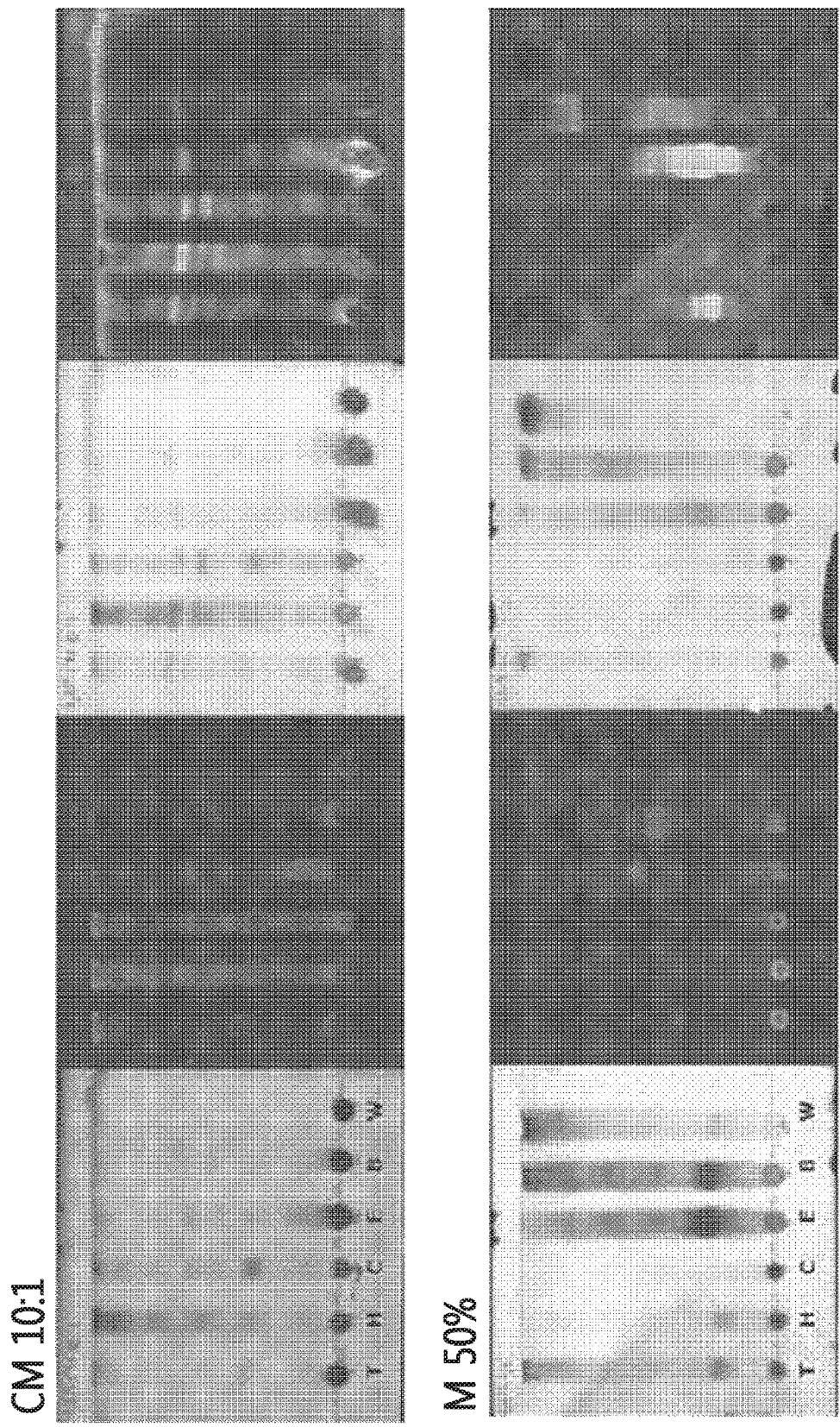
FIG. 1 shows the results of thin layer chromatography (TLC) analysis of a *Lagerstroemia ovalifolia* extract and a fraction thereof.
T: methanol extract of *Lagerstroemia ovalifolia*.
H: n-hexane fraction of *Lagerstroemia ovalifolia*.
C: chloroform fraction of *Lagerstroemia ovalifolia*.
E: acetyl acetate fraction of *Lagerstroemia ovalifolia*.
B: butanol fraction of *Lagerstroemia ovalifolia*.
W: water fraction of *Lagerstroemia ovalifolia*.

In one aspect, the present invention provides a pharmaceutical composition for preventing or treating inflammatory diseases or asthma comprising a *Lagerstroemia ovalifolia* extract or a fraction thereof as an active ingredient.

As used herein, the term "inflammation" refers to a pathological condition of abscess formed by the invasion of foreign infectious agents (bacteria, fungi, virus, and various allergens). As used herein, the term "inflammatory disease" refers to a disease that involves inflammation as described above.

The inflammatory disease may be one or more selected from the group consisting of systemic lupus erythematosus, scleroderma, ulcerative colitis, Crohn's disease, atopic dermatitis, psoriasis, anaphylaxis, dermatitis, diabetic retinopathy, retinitis, macular degeneration, uveitis, conjunctivitis, arthritis, rheumatoid arthritis, ankylsoing spondylitis, osteoarthritis, osteoporosis, allergy, diabetes, diabetic nephropathy, nephritis, Sjögren's syndromes, autoimmune pancreatitis, periodontal disease, asthma, graft-versus-host disease, chronic pelvic inflammatory disease, endometritis, nasitis, tonsillitis, otitis media, pharyngitis, cystitis, and chronic prostatitis, but diseases to which the present invention can be applied are not limited thereto.

Asthma is a kind of allergic disease which is caused by the allergic inflammatory response of a bronchus in the lung in a state in which the bronchus is sensitive. Allergy is a phenomenon in which a living body coming into contact with any foreign material shows abnormal responses to the material.

For the purpose of the present invention, a *Lagerstroemia ovalifolia* extract according to the present invention or a fraction thereof are used to prevent or treat inflammatory diseases or asthma.

As used herein, the term "preventing" refers to all actions that inhibit symptoms of inflammatory diseases or asthma or delay the development of inflammatory diseases or asthma by administering the composition of the present invention. As used herein, the term "treating" refers to all actions that alleviate or beneficially change symptoms of inflammatory diseases or asthma' by administering the composition of the present invention.

The *Lagerstroemia ovalifolia* extract according to the present invention can be prepared using any solvent known in the art. Preferably, it can be prepared using water, a $C_1$-$C_4$ alcohol, or a mixed solvent thereof. More preferably, it can be prepared using methanol.

The *Lagerstroemia ovalifolia* extract according to the present invention may comprise one or more selected from among an extract obtained by an extraction process, a dilution or concentrate of the extract, a dried material obtained by drying the extract, and a crude or purified form thereof.

The *Lagerstroemia ovalifolia* extract according to the present invention can be prepared using conventional methods known in the art, including ultrasonic extraction, filtration and reflux extraction. *Lagerstroemia ovalifolia* that is used in the present invention may be commercially available or may be collected or cultivated in nature.

As used herein, the term "fraction" refers to a material obtained by a fractionation process that separates a specific component or a specific group from a mixture of various components.

Examples of a solvent that is used to prepare the *Lagerstroemia ovalifolia* extract comprise, but are not limited to, conventional fractionation solvents known in the art, for example, polar solvents such as $C_1$-$C_4$ alcohols (e.g., methanol, ethanol, butanol, etc.), non-polar solvents such as hexane, ethyl acetate, chloroform and dichloromethane, or mixtures thereof.

A fraction of the *Lagerstroemia ovalifolia* extract according to the present invention may comprise those obtained by additionally performing a purification process. For example, the scope of a fraction of the *Lagerstroemia ovalifolia* extract according to the present invention comprising fractions obtained by passing the *Lagerstroemia ovalifolia* extract through an ultrafiltration membrane having a specific molecular weight cut-off value, and fractions obtained by additionally performing various purification processes using various chromatographic systems (manufactured for separation based on size, charge, hydrophobicity or affinity), etc.

In addition, the *Lagerstroemia ovalifolia* extract according to the present invention or a fraction thereof can be prepared in the form of powder by additional processes such as vacuum distillation and freeze drying or hot-air drying.

The composition of the present invention may comprise, in addition to the *Lagerstroemia ovalifolia* extract or a fraction thereof, one or more active ingredients showing functions equal or similar to the extract or fraction.

The pharmaceutical composition of the present invention may comprise a pharmaceutically acceptable carrier. The composition comprising the pharmaceutically acceptable carrier may be provided as various oral or parenteral formulations. The composition of the present invention may be formulated with commonly used diluents or excipients, such as fillers, extenders, binders, wetting agents, disintegrants, surfactants, etc. Solid formulations for oral administration include tablets, pills, powders, granules, capsules and the like, and such solid formulations comprise, in addition to the composition, at least one excipient, for example, starch, calcium carbonate, sucrose, lactose or gelatin. In addition to simple excipients, lubricants such as magnesium stearate or talc may also be used. Liquid formulations for oral administration include suspensions, solutions, emulsions, and syrup, and may comprise various excipients, for example, wetting agents, flavoring agents, aromatics and preservatives, in addition to water and liquid paraffin, which are frequently used simple diluents. Formulations for parenteral administration include sterilized aqueous solutions, non-aqueous solutions, suspensions, emulsions, freeze-dried preparations, and suppositories. As non-aqueous solvents or suspending agents, propylene glycol, polyethylene glycol, plant oils such as olive oil, injectable esters such as ethyl oleate, and the like can be used. As the base of the suppositories, witepsol, Macrogol, Tween 61, cacao butter, laurin fat, glycerogelatin and the like can be used. The pharmaceutical composition may have any one formulation selected from the group consisting of tablets, pills, powders, granules, capsules, suspensions, solutions, emulsions, syrups, sterilized aqueous solutions, non-aqueous solutions, freeze-dried formulations, and suppositories.

The pharmaceutical composition of the present invention is administered in a pharmaceutically effective amount. As used herein, the term "pharmaceutically effective amount" refers to an amount sufficient to treat diseases, at a reasonable benefit/risk ratio applicable to any medical treatment. The effective dosage level of the composition may be determined depending on the subject's type, the disease severity, the subject's age and sex, the type of infected virus, the activity of the drug, sensitivity to the drug, the time of administration, the route of administration, excretion rate, the duration of treatment, drugs used in combination with the composition, and other factors known in the medical field. The pharmaceutical composition of the present invention may be administered individually or in combination with other therapeutic agents, and may be administered sequentially or simultaneously with conventional therapeutic agents. The composition can be administered in a single or multiple dosage form. It is important to administer the composition in the minimum amount that can exhibit the maximum effect without causing side effects, in view of all the above-described factors, and this amount can be easily determined by a person skilled in the art.

The composition of the present invention may be used alone or in combination with surgery, hormonal therapy, drug therapy, and methods that use biological response regulators, in order to prevent or treat inflammatory diseases or asthma.

In another aspect, the present invention provides the use of a *Largerstroimia ovalifolia* extract or a fraction thereof for preventing or treating inflammatory diseases or asthma. Herein, the *Largerstroimia ovalifolia* extract, the fraction, the inflammatory diseases, the asthma, the preventing and the treating are as described above.

In still another aspect, the present invention provides a method for treating inflammatory diseases or asthma, the method comprising administering to a subject in need thereof a pharmaceutically effective amount of a pharmaceutical composition comprising a *Largerstroimia ovalifolia* extract or a fraction thereof as an active ingredient.

As used herein, the term "subject" is meant to include all animals, including humans, who have or are at risk of developing inflammatory disease or asthma. Herein, the *Largerstroimia ovalifolia* extract, the fraction, the inflammatory disease, the asthma, the preventing and the treating are as described above.

The composition of the present invention may be administered by any general route, as long as it can reach a desired tissue. It may be administered intraperitoneally, intravenously, intramuscularly, subcutaneously, intradermally, orally, intranasally, intrapulmonarily or intrarectally depending on the intended use thereof, but is not limited thereto.

In an example of the present invention, macrophages were treated with various concentrations of a *Largerstroimia ovalifolia* extract and analyzed by an MTT assay. As a result, it was found that the *Largerstroimia ovalifolia* extract was not cytotoxic even at a concentration of 30 µg/ml, suggesting that the *Largerstroimia ovalifolia* extract can be safely used as an agent for preventing or treating inflammatory diseases (Tables 1 and 2).

Figure 3:
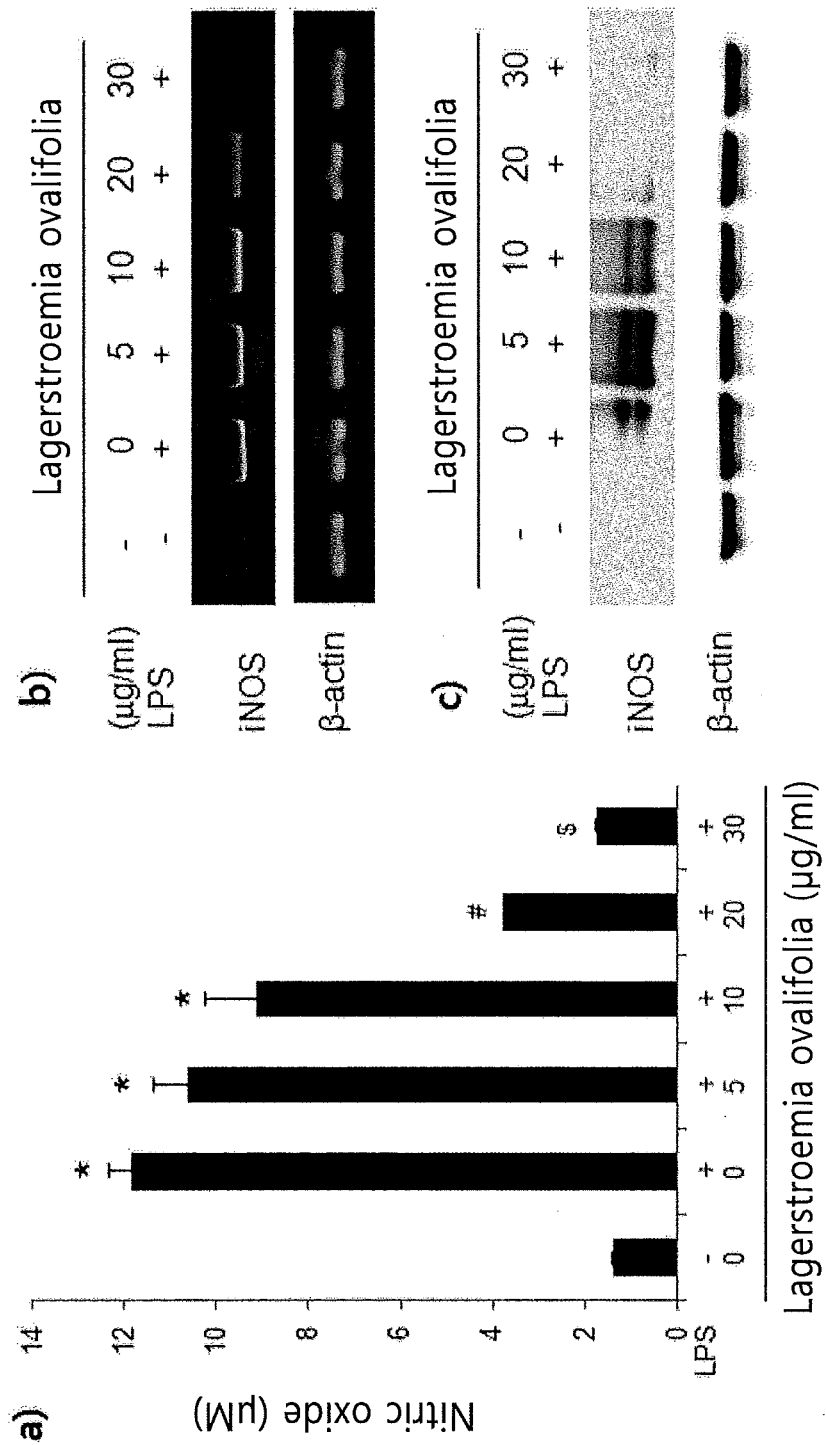
FIG. 3 shows the effects of a *Lagerstroemia ovalifolia* extract on the inhibition of LPS-induced NO production and iNOS expression in RAW264.7 cells.
Figure 4:
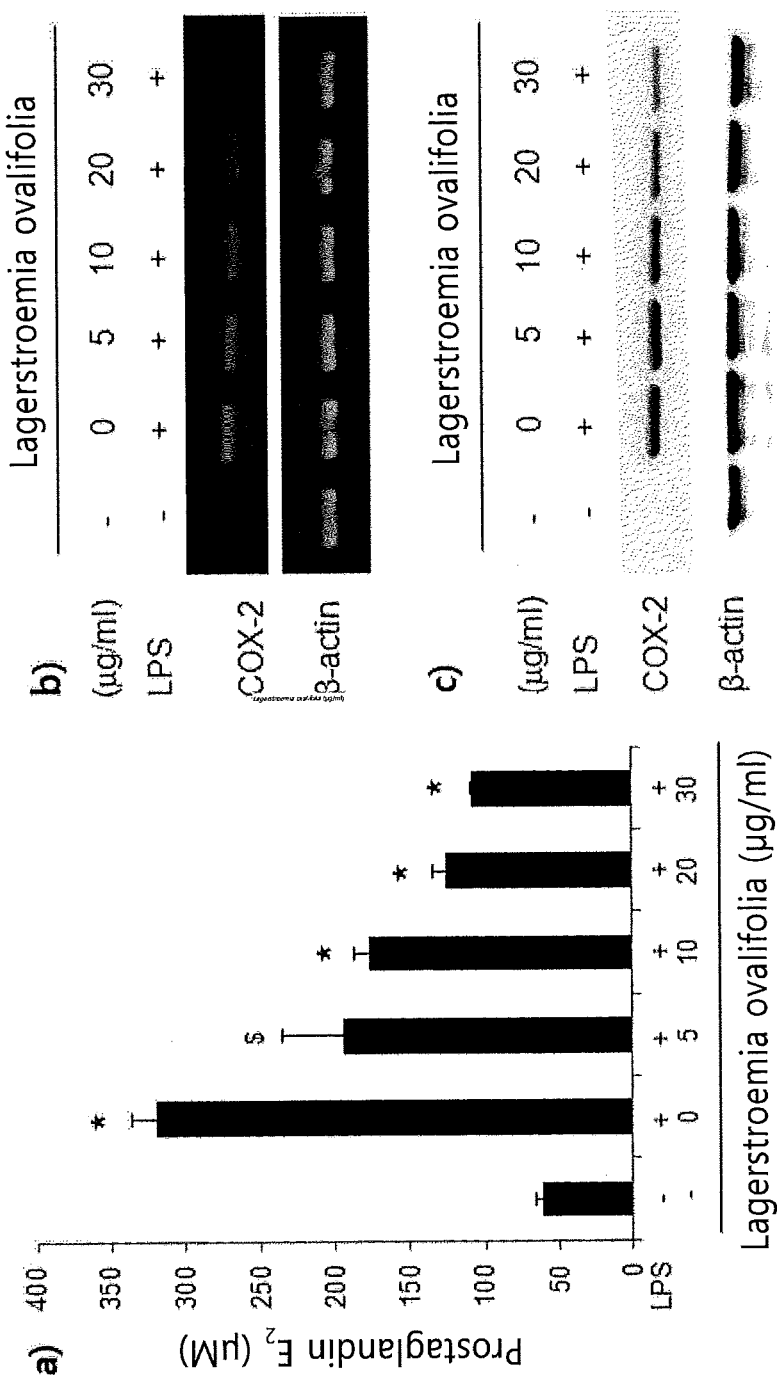
FIG. 4 shows the effects of a *Lagerstroemia ovalifolia* extract on the inhibition of LPS-induced $PGE_2$ production and COX-2 expression in RAW264.7 cells.
Figure 5:
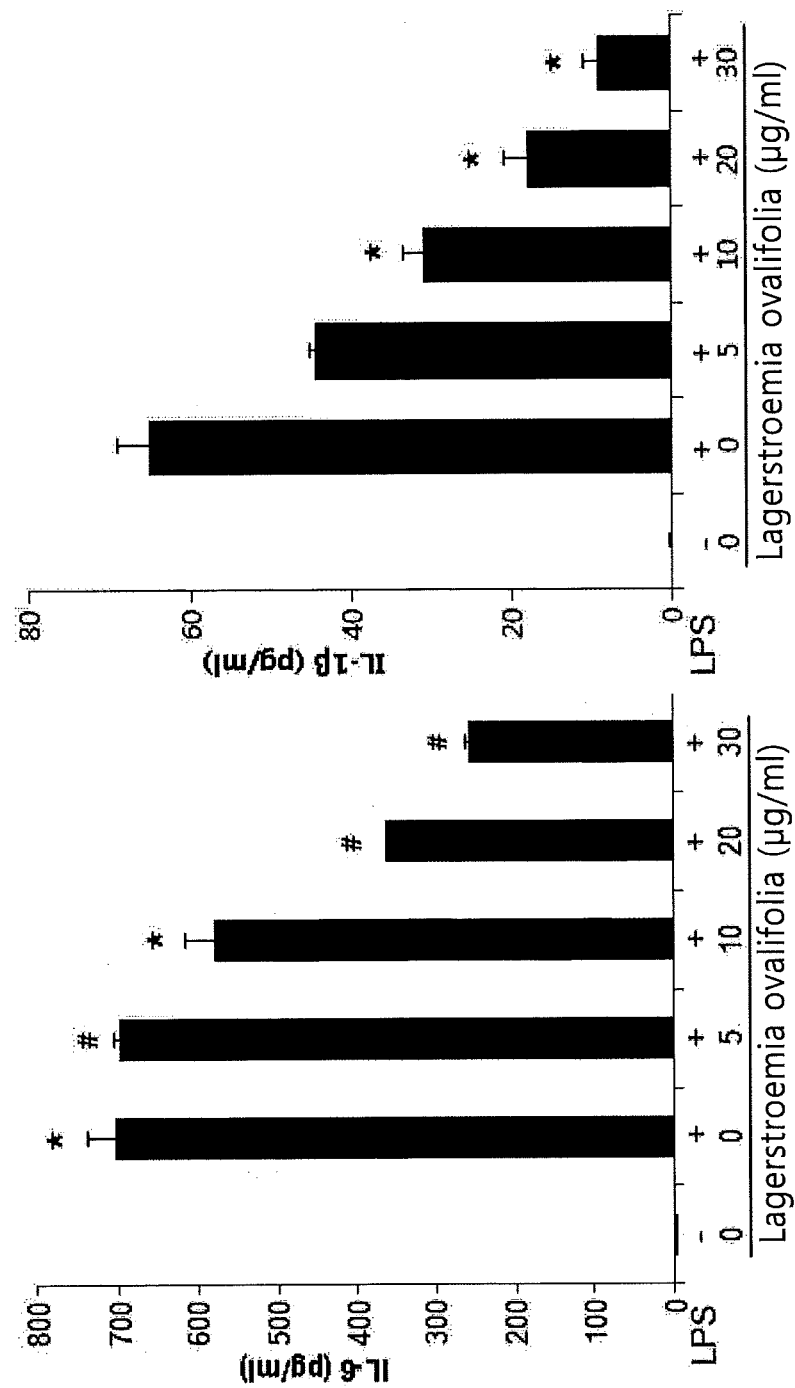
FIG. 5 shows the effects of a *Lagerstroemia ovalifolia* extract on the inhibition of the LPS-induced expression of IL-6 and IL-1 beta in RAW264.7 cells, in which (*) indicates P<0.005 versus positive control, and (#) indicates P<0.0005 versus positive control. First bar from the left: negative control group administered with 0.15% DMSO alone; second bar from the left: positive control group treated with 0.5 μg/ml of LPS to induce inflammation; and the remaining bar: test groups treated with various concentrations of a *Lagerstroemia ovalifolia* extract, and then treated with LPS to induce inflammation.

In another example of the present invention, the inhibitory activities of the *Largerstroimia ovalifolia* extract against inflammatory mediators were examined. As a result, it was found that the *Largerstroimia ovalifolia* extract showed inhibitory activities against (a) the production of nitric oxide (NO) in macrophages, (b) the expression of iNOS (inducible nitric oxide synthase) in macrophages, (c) the production of $PGE_2$ (prostaglandin $E_2$) in macrophages, (d) the expression of COX-2 (cyclooxygenase-2), (e) the production of IL-6, and (f) the production of IL-1β, suggesting that the *Largerstroimia ovalifolia* extract has excellent effects on the prevention and treatment of inflammatory diseases (FIGS. 3 to 5).

In still another example of the present invention, the effects of treatment with the *Largerstroimia ovalifolia* extract or a fraction thereof in ovalbumin-induced asthma mouse models were examined. As a result, it was found that the extract or fraction had the effects of 1) alleviating airway hypersensitivity and inhibiting the infiltration of inflammatory cells into a bronchus, 2) reducing the level of cytokines in bronchoalveolar lavage fluid, 3) inhibiting the secretion of blood immunoglobulin, and 4) inhibiting the mucous secretion of globlet cells, suggesting that the *Largerstroimia ovalifolia* extract or a fraction thereof is useful against not only inflammatory diseases, but also asthma diseases (FIGS. 6 to 11).

The composition of the present invention may be used together with other agents useful for the treatment, prevention, inhibition or alleviation of inflammatory diseases, asthma, and other diseases or conditions as mentioned above.

Other agents or drugs may be administered simultaneously or sequentially with the composition of the present invention in the ways and amounts in which they are commonly used. When the composition of the present invention is to be used simultaneously with one or more drugs, pharmaceutical compositions comprising other drugs are preferably added to the composition of the present invention. Thus, the pharmaceutical composition of the present invention comprises one or more other active ingredients or therapeutic agents.

Examples of other therapeutic agents that may be combined with the composition compound of the present invention, either administered separately or in the same pharmaceutical compositions, include, but are not limited to, (a) VLA-4 antagonists; (b) steroids such as beclomethasone, methylprednisolone, betamethasone, prednisone, prenisolone, triamcinolone, dexamethasone, fluticasone, flunisolide, and corticosteroid analogs such as hydrocortisone and budesonide; (c) immunosuppressants such as cyclosporine (cyclosporine A, Sandimmune®, Neorals®), tacrolimus (FK-506, Prograf®), rapamycin, sirolimus, Rapamune®, and other FK-506 type immunosuppressants, and mycophenolate, for example, mycophenolate mofetil (CellCept®); (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine, pyrilamine, astemizole, terfenadine, loratadine, cetirizine, fexofenadine, descarboethoxyloratadine, and the like; (e) non-steroidal anti-asthmatics such as β-agonists (e.g., terbutaline, metaproterenol, fenoterol, isoetharine, albuterol, salmeterol, bitolterol and pirbuterol) and combinations of β-agonist steroids (e.g., salmeterol-fluticasone (Advairo®), formoterol-budesonid (Symbicort®), theophylline, cromolyn, cromolyn sodium, nedocromil, atropine, ipratropium, ipratropium bromide, leukotriene antagonists (e.g., zafirlukast, montelukast, montelukast sodium (Singulair®), pranlukast, iralukast, pobilukast and SKB-106, 203), leukotriene biosynthesis inhibitors (zileuton, BAY-1005); (f) non-steroidal antiinflammatory agents (NSAIDs) such as propionic acid derivatives (e.g., alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid and tioxaprofen), acetic acid derivatives (e.g., indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac), fenamic acid derivatives (e.g., flufenamic acid, meclofenamic acid, mefenamic acid, niflumic acid and tolfenamic acid), biphenylcarboxylic acid derivatives (e.g., diflunisal and flufenisal), oxicams (e.g., isoxicam, piroxicam, sudoxicam and tenoxican), salicylates (e.g., acetyl salicylic acid, and sulfasalazine), and pyrazolones (e.g., apazone, bezpiperylon, feprazone, mofebutazone, oxyphenbutazone and phenylbutazone); (g) cyclooxygenase-2 (COX-2) inhibitors such as celecoxib (Celebrex®) and rofecoxib (Vioxx®); (h) inhibitors of phosphodiesterase type IV (PDE-IV); (i) other PGD2 receptor antagonists, particularly DP antagonists; (j) opioid analgesics such as codeine, fentanyl, hydromorphone, levorphanol, meperidine, methadone, morphine, oxycodone, oxymorphone, propoxyphene, buprenorphine, butorphanol, dezocine, nalbuphine and pentazocine; (k) cholesterol lowering agents such as HMG-CoA reductase inhibitors (e.g., lovastatin, simvastatin, pravastatin, fluvastatin, atorvastatin and other statins), bile acid sequestrants (e.g., cholestyramine and colestipol), vitamin $B_3$ (also known as nicotinic acid, or niacin), vitamin $B_6$ (pyridoxine), vitamin $Bi_t$ (cyanocobalamin), fibric acid derivatives (e.g., gemfibrozil, clofibrate, fenofibrate and benzafibrate), probucol, nitroglycerin, and inhibitors of cholesterol absorption (e.g., beta-sitosterol and acylCoA-cholesterol acyltransferase (ACAT) inhibitors such as melinamide), HMG-CoA synthase inhibitors, squalene epoxidase inhibitors and squalene synthetase inhibitors; (l) antithrombotic agents, such as thrombolytic agents (e.g., streptokinase, alteplase, anistreplase and reteplase), heparin, hirudin and warfarin derivatives, beta-blockers (e.g., atenolol), beta-adrenergic agonists (e.g., isoproterenol), ACE inhibitors and vasodilators (e.g., sodium nitroprusside, nicardipine hydrochloride, nitroglycerin and enaloprilat); (m) anti-diabetic agents such as insulin and insulin mimetics, sulfonylureas (e.g., glyburide, meglinatide), biguanides, for example, metformin (Glucophage®), α-glucosidase inhibitors (acarbose), thiazolidinone compounds, for example, rosiglitazone (Avandia®), troglitazone (Rezulin®), ciglitazone, pioglitazone (Actors) and englitazone; (n) preparations of interferon beta (interferon β-1α, interferon β-1β); (o) gold compounds such as auranofin and aurothioglucose; (p) TNF inhibitors such as etanercept (Enbrel), antibody therapies such as orthoclone (OKT3), daclizumab (Zenapax®), basiliximab (Simulect®), infliximab (Remicade®) and D2E6 TNF antibody; (q) lubricants or emollients such as Vaseline and lanolin, keratolytic agents, vitamin D3 derivatives (e.g., calcipotriene or calcipotriol (Dovonex®), PUVA, anthralin (Drithrocreme®), etretinate (Tegisono®) and isotretinoin; (r) multiple sclerosis therapeutic agents such as interferon β-1β, (Betaseron®), interferon β-1α (Avonex®), azathioprine (Imurek®, Imuran®), glatiramer acetate (Capoxone®), a glucocorticoid (e.g., prednisolone) and cyclophosphamide; (s) other compounds such as 5-aminosalicylic acid and prodrugs thereof; (t) DNA-alkylating agents (e.g., cyclophosphamide, ifosfamide), antimetabolites (e.g., azathioprene, 6-mercaptopurine, methotrexate, a folate antagonist, and 5-fluorouracil, a pyrimidine antagonist), microtubule disruptors (e.g., vincristine, vinblastine, paclitaxel, colchicine, nocodazole and vinorelbine), DNA intercalators (e.g., doxorubicin, daunomycin and cisplatin), DNA synthesis inhibitors such as hydroxyurea, DNA cross-linking agents, e.g., mitomycin C, hormone therapy (e.g., tamoxifen, and flutamide), and cell proliferation inhibitors, for example, imatinib (STI571, Gleevec®) and rituximab (Rituxan®). The weight ratio of a second active ingredient to the composition of the present invention may vary and be determined by those skilled in the art depending on the effective amount of each component.

In still another aspect, the present invention provides a health functional food for preventing or ameliorating inflammatory diseases or asthma comprising a *Lagerstroemia ovalifolia* extract or a fraction thereof as an active ingredient.

If the *Lagerstroemia ovalifolia* extract or a fraction thereof is used as a food additive, it can be added alone in combination with other foods or food ingredients and may be used appropriately according to conventional methods.

The content of the active ingredient can be suitably determined depending on the purpose of use (prophylactic, health or therapeutic treatment).

There is no particular limit to the kind of food. Examples of foods to which the *Lagerstroemia ovalifolia* extract or a fraction thereof can be added include meats, sausages, bread, chocolate, candies, snack, confectionery, pizza, noodles, gum, dairy products including ice cream, various soups, beverages, teas, drinks, alcoholic beverages and multi-vitamin preparations. The foods include all health foods in a conventional sense.

In addition, the health functional food of the present invention may comprise various nutrients, vitamins, electrolytes, flavoring agents, colorants, pectic acid or its salt, alginic acid or its salt, organic acids, protective colloidal thickeners, pH adjusters, stabilizers, preservatives, glycerin, alcohol, carbonating agents used in carbonated drinks, etc. Additionally, the health functional food of the present invention may comprise fruit flesh for the preparation of natural fruit juices, fruit juice beverages and vegetable juices.

In still another aspect, the present invention provides a feed additive for preventing or ameliorating inflammatory diseases or asthma comprising a *Lagerstroemia ovalifolia* extract or a fraction thereof.

The feed additive can prevent inflammation or asthma by allowing poultry, livestock or the like to take it constantly, and can treat developed inflammation or asthma.

In a preferred embodiment, the feed additive of the present invention may comprise 0.1-20 wt % of the *Lagerstroemia ovalifolia* extract or a fraction or active fraction thereof, 0.001-0.01 wt % of lipase, 1-20 wt % of tricalcium phosphate, 0.01-0.1 wt % of vitamin E, 1-10 wt % of enzyme powder, 0.1-10 wt % of lactic acid bacteria, 0.01-10 wt % of a *Bacillus* culture and 20-90 wt % of glucose, but is not limited thereto. In addition, any feed additive may be the feed additive of the present invention, as long as it comprises an effective amount of the *Lagerstroemia ovalifolia* extract or a fraction or active fraction thereof.

As used herein, the term "effective amount" refers to an amount that can prevent inflammation or asthma or treat developed inflammation or asthma by allowing poultry, livestock or the like to take it constantly. The effective amount is preferably an amount that does not cause an adverse effect exceeding the benefit of addition.

The feed additive of the present invention may comprise known carriers, stabilizers and the like. It may, if necessary, comprise various nutrients such as vitamins, amino acids or minerals, antioxidants, antibiotics, antibacterial agents, and other additives. It may be provided in the form of powders, granules, pellets, suspensions or the like. The feed additive of the present invention may be fed alone or in a mixture with feed to poultry and livestock.

MODE FOR INVENTION

Hereinafter, the present invention will be described in further detail with reference to examples and experimental examples. It is to be understood, however, that these examples are for illustrative purposes only and are not intended to limit the scope of the present invention.

Preparation Example 1

Preparation of Extracts of Plants Belonging to the Genus *Lagerstroemia*

A methanol extract of *Lagerstroemia ovalifolia* Teijsm. & Binn. was purchased from the International Biological Material Research Center located at the Korea Research Institute of Bioscience and Biotechnology. A voucher specimen (KRIB 0038535) has been deposited at the herbarium of the Korea Research Institute of Bioscience and Biotechnology. In an extraction process, 10 kg of *Lagerstroemia ovalifolia* Teijsm. & Binn. was collected and dried with a dryer (50~55° C.) in order to facilitate powdering. 10.8 kg of the powdered sample was added to 200 l of methanol and then extracted at room temperature. The extract was filtered and concentrated under reduced pressure, thereby obtaining 1,030 g of a *Lagerstroemia ovalifolia* extract. In the following experiment, the *Lagerstroemia ovalifolia* extract was dissolved in DMSO (dimethyl sulfoxide) at a concentration of 20 mg/ml, and then diluted to various concentrations before use.

In addition, methanol extracts of *Lagerstroemia calyculata* Kurz, *Lagerstroemia chekiangensis* Cheng, *Lagerstroemia floribunda* Jack sec. Griff., *Lagerstroemia flos-reginae* Retz., *Lagerstroemia indica* L., *Lagestroemia indica* for. *latifolia* Koehne, *Lagerstroemia lecomtei* Gagnep., *Lagerstroemia loudonii* Teysm. & Binn., *Lagerstroemia macrocarpa* Wall. ex Kurz, *Lagerstroemia ovalifolia* Teijsm. & Binn., *Lagerstroemia speciosa* (L.) Pers., *Lagerstroemia tomentosa* C. Presl, *Lagerstroemia venusta* Wall. ex C. B. Clarke and *Lagerstroemia villosa* Wall. ex Kurz, which are plants belonging to the genus *Lagerstroemia*, were all purchased from the International Biological Material Research Center located at the Korea Research Institute of Bioscience and Biotechnology. Each of the dried extracts were dissolved in a DMSO solvent at a concentration of 20 mg/ml and used in each experiment.

Preparation Example 2

Preparation of Fractions of Extracts of Plants Belonging to the Genus *Lagerstroemia*

1.0 g of the methanol extract of *Lagerstroemia ovalifolia* prepared in Preparation Example 1 was added to and suspended in 50 ml of distilled water. The same amount of n-hexane was added to and mixed with the suspension, and the mixture was separated into an n-hexane soluble fraction and a water soluble fraction. This procedure was repeated three times, and the resulting material was filtered and concentrated under reduced pressure, thereby obtaining 100.5 mg of an n-hexane fraction. Next, the same amount of chloroform was added to the aqueous layer remaining after removal of the n-hexane fraction, and the same procedure as described above was performed, thereby obtaining 73.6 mg of a chloroform fraction. Next, the same amount of ethyl acetate was added to the remaining aqueous layer, and the same procedure as described above was performed, thereby obtaining 91.9 mg of an ethyl acetate fraction. Next, the same amount of butanol was added to the remaining aqueous layer, and the same procedure as described above was performed, thereby obtaining 138.2 mg of a butanol fraction. Next, the remaining aqueous layer was concentrated to obtain 395.6 mg of a water fraction.

Example 1

TLC Analysis of *Lagerstroemia ovalifolia* Extract and Fractions

Each of the methanol extract of *Lagerstroemia ovalifolia* and fractions thereof, prepared in Preparation Examples 1 and 2, was dissolved in methanol at a concentration of 10 mg/ml, and then analyzed by silica gel thin-layer chromatography (TLC Silica gel 60 $F_{254}$, Merck). Thin-layer chromatography is a primary method for analyzing the composition of a mixture and is used in initial separation and analysis based on the difference in polarity of a developing solvent. As a developing solvent, a mixed solvent of chloroform:methanol (10:1) was used. In addition, silica gel reverse-phase chromatography (TLC Silica gel 60 RP-18 $F_{254}$5, Merck) was performed using 50% methanol as a developing solvent, and the results of the chromatography are shown in FIG. 1.

Example 2

UPLC Analysis of *Lagerstroemia ovalifolia* Extract and Fractions

Figure 2:
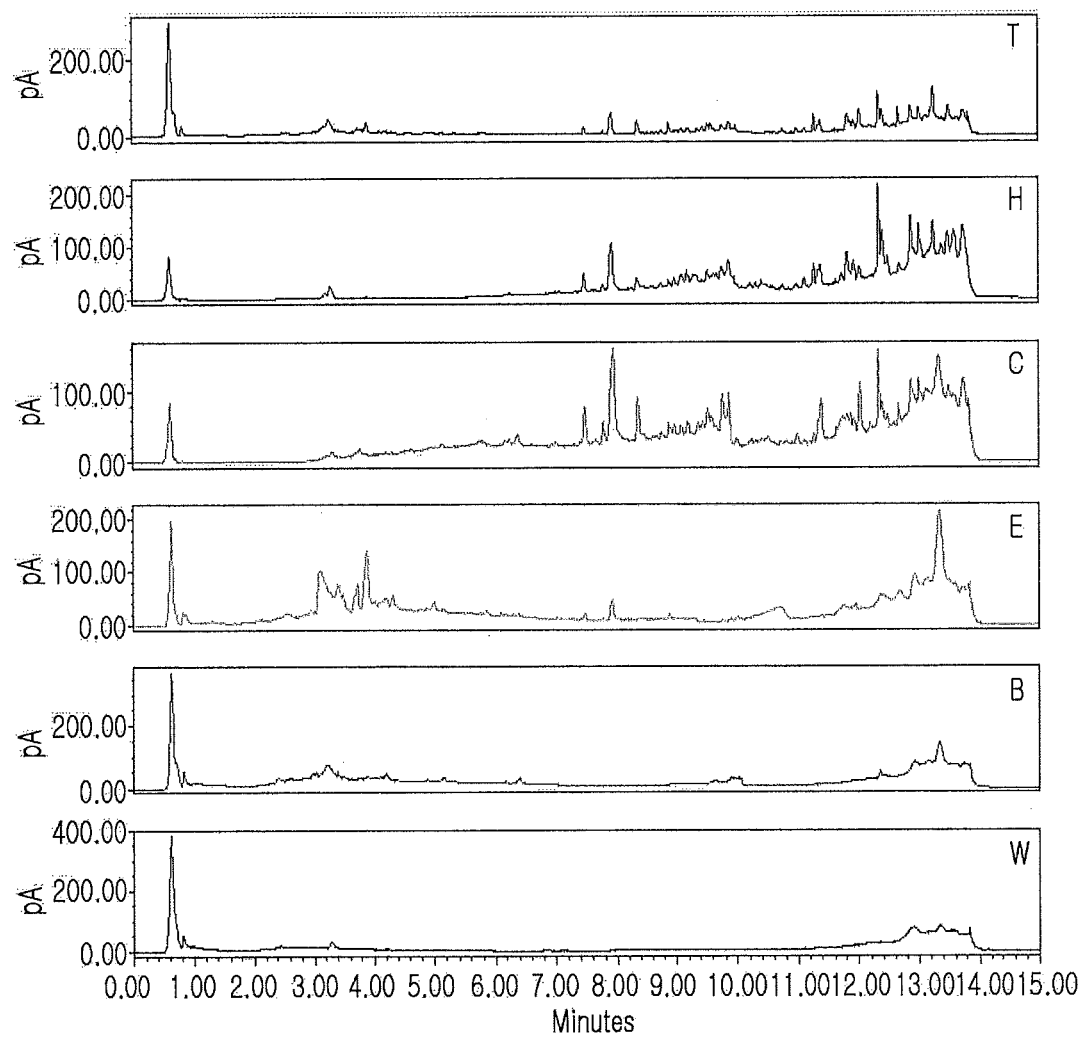
FIG. 2 shows the results of analyzing a *Lagerstroemia ovalifolia* extract and a fraction thereof using a charged aerosol detector (CAD).

Each of the methanol extract of *Lagerstroemia ovalifolia* and fractions thereof, prepared in Preparation Examples 1 and 2, was dissolved in methanol at a concentration of 10 mg/ml, and then filtered through a 0.2-μm membrane filter. UPLC analysis was performed using a Waters Acquity UPLC system and ACQUITY UPLC™ BEHC$_{18}$ (10 mm×2.1 mm, I.D., 1.7 μm, Waters, USA) as a column at 35° C. Mobile phase A consisted of water and formic acid (100:0.1, v/v), and mobile phase B consisted of acetonitrile and formic acid (100:0.1, v/v). In the analysis, mobile phase was maintained at 10% for 1 min, then increased to 50% up to 7 min, increased to 100% up to 12 min, then maintained at 100% up to 13 min, decreased to 10% up to 13.1 min, and stabilized to 10% up to 15 min. The flow rate of the mobile phase was 0.4 ml/min, and the amount of sample injected was 10 μl. Also, using CAD (Charged Aerosol Detector) as a detector, the relative contents and separation extents of materials separated from the UPLC were analyzed in a chromatographic manner (FIG. 2).

Experimental Example 1

Evaluation of Cytotoxicity of Extracts of Plants Belonging to the Genus *Lagerstroemia*

Mouse Raw264.7 macrophages were suspended in 5% fetal bovine serum-containing DMEM (Dulbecco's Modified Eagle Medium, Gibco) at a concentration of $1 \times 10^5$ cells/ml, and 100 μl of the cell suspension was seeded into each well of a 96-well plate. After 4 hours, the cells were treated with 0, 5, 10, and 30 μg/ml of the methanol extract of *Lagerstroemia ovalifolia*. In addition, each of extracts of other plants belonging to the genus *Lagerstroemia* was used at a concentration of 20 μg/ml to treat the cells. After 24 hours of culture, 5 mg/ml of MTT solution was added to each well in an amount of 10 μl, and then the cells were further cultured for 4 hours. After completion of the culture, the supernatant was removed, and then 100 μl of DMSO was added to each well, and the absorbance at 570 nm was measured. Cell viability was calculated according to the following equation based on 100% for a negative control group treated with 0.15% DMSO.

Cell viability (%)=[($OD_{570\ nm}$ value of group treated with extract)/($OD_{570\ nm}$ value of negative control group)]×100    Equation 1

As a result, as can be seen in Table 1 below, among the extracts of plants belonging to the genus *Lagerstroemia*, the extracts of *Lagerstroemia ovalifolia* Teijsm. & Binn. and *Lagerstroemia speciosa* (L.) Pers.) showed no cytotoxicity. In addition, as can be seen in Table 2 below, the methanol.

extract of *Lagerstroemia ovalifolia* showed no cytotoxicity even when it was used at a concentration of 30 μg/ml.

TABLE 1

| Sample (20 μg/ml) | Viability (%, Ave ± SD) |
|---|---|
| *Lagerstroemia calyculata* Kurz | 88.39 ± 8.45 |
| *Lagerstroemia chekiangensis* Cheng | 68.82 ± 4.27 |
| *Lagerstroemia floribunda* Jack sec. Griff. | 81.74 ± 5.07 |
| *Lagerstroemia flos-reginae* Retz. | 70.21 ± 5.38 |
| *Lagerstroemia indica* L. | 92.13 ± 5.41 |
| *Lagerstroemia indica for. latifolia* Koehne | 50.72 ± 7.18 |
| *Lagerstroemia lecomtei* Gagnep. | 63.82 ± 7.11 |
| *Lagerstroemia loudonii* Teysm. & Binn. | 99.82 ± 5.32 |
| *Lagerstroemia macrocarpa* Wall. ex Kurz | 58.30 ± 11.67 |
| *Lagerstroemia ovalifolia* Teijsm. & Binn. | 102.54 ± 11.69 |
| *Lagerstroemia speciosa* (L.) Pers. | 102.54 ± 4.65 |
| *Lagerstroemia tomentosa* C. Presl | 42.71 ± 6.05 |
| *Lagerstroemia venusta* Wall. ex C. B.Clarke | 53.73 ± 5.99 |
| *Lagerstroemia villosa* Wall. ex Kurz | 98.69 ± 1.17 |

TABLE 2

| Sample (20 μg/ml) | | Viability (%, Ave ± SD) |
|---|---|---|
| Negative control | | 100.00 ± 5.85 |
| *Lagerstroemia ovalifolia* Teijsm. & Binn. | 5 μg/ml | 110.30 ± 10.50 |
| *Lagerstroemia ovalifolia* Teijsm. & Binn. | 10 μg/ml | 106.38 ± 6.00 |
| *Lagerstroemia ovalifolia* Teijsm. & Binn. | 20 μg/ml | 118.02 ± 6.25 |
| *Lagerstroemia ovalifolia* Teijsm. & Binn. | 30 μg/ml | 123.24 ± 2.68 |

Experimental Example 2

Inhibitory Effects of Extracts of Plants Belonging to the Genus *Lagerstroemia* Against Production of Nitric Oxide In order to examine inhibitory effects against inflammation artificially induced by treating Raw264.7 cells with LPS, the production of inducible nitric oxide (NO) was measured in the following manner. 5% fetal bovine serum was added to DMEM medium comprising no phenol-Red, and $1\times10^5$ cells were suspended in the medium and seeded into a 96-well plate. After 4 hours of adherent culture, the cells were treated with 0, 5, 10, 20 and 30 μg/ml of the methanol extract of *Lagerstroemia ovalifolia*. In addition, each of extracts of other plants belonging to the genus *Lagerstroemia* was used at a concentration of 20 μg/ml to treat the cells. After 1 hour of culture, the cells were treated with 0.5 μg/ml of LPS (lipopolysaccharide, Sigma), followed by culture for 24 hours. Next, 100 μl of the supernatant was recovered and added to a fresh 96-well plate, and the same amount of Griess reagent (Sigma) was added thereto and allowed to react at room temperature for 10 minutes. Then, the absorbance at a wavelength of 540 was measured using a microplate reader (Bio-Rad). A calibration curve was plotted using sodium nitrite, and based on this curve, the production of nitric oxide in the culture was determined. Also, the inhibition of NO production in the group treated with each sample relative to 100% for NO production in group treated with LPS was expressed as percentage (see the following equation 2), and the results are shown in Table 3 below and FIG. 3.

Percent inhibition of NO production=[1−
[($OD_{540\ nm}$ value of group treated with sample)/
($OD_{540\ nm}$ value of group with LPS)]]×100    Equation 2

As a result, as can be seen in Table 3 above, the percent inhibition of nitric oxide was 31.89±3.47% for *Lagerstroemia indica* L. and 14.17±1.49% for *Lagerstroemia speciosa* (L.) Pers. However, it was 71.15±0.66% for *Lagerstroemia ovalifolia* Teijsm. & Binn., suggesting that the extract of *Lagerstroemia ovalifolia* has significantly high inhibitory activity against NO production compared to other plants belonging to the genus *Lagerstroemia*.

TABLE 3

| Sample (20 μg/ml) | Inhibition (%, Ave ± SD) |
|---|---|
| *Lagerstroemia calyculata* Kurz | 29.96 ± 0.73 |
| *Lagerstroemia chekiangensis* Cheng | 11.34 ± 1.23 |
| *Lagerstroemia floribunda* Jack sec. Griff. | 10.42 ± 7.59 |
| *Lagerstroemia flos-reginae* Retz. | −0.68 ± 13.04 |
| *Lagerstroemia indica* L. | 31.89 ± 3.47 |
| *Lagerstroemia indica for. latifolia* Koehne | 10.90 ± 4.32 |
| *Lagerstroemia lecomtei* Gagnep. | 18.86 ± 2.07 |
| *Lagerstroemia loudonii* Teysm. & Binn. | 17.26 ± 2.25 |
| *Lagerstroemia macrocarpa* Wall. ex Kurz | 3.28 ± 8.11 |
| *Lagerstroemia ovalifolia* Teijsm. & Binn. | 71.15 ± 0.66 |
| *Lagerstroemia speciosa* (L.) Pers. | 14.17 ± 1.49 |
| *Lagerstroemia tomentosa* C. Presl | 15.30 ± 5.10 |
| *Lagerstroemia venusta* Wall. ex C. B. Clarke | 10.29 ± 1.23 |
| *Lagerstroemia villosa* Wall. ex Kurz | 16.13 ± 2.66 |

As shown in FIG. 3a), treatment with LPS significantly increased the production of nitric oxide, but the production of nitric oxide in the group treated with the methanol extract of *Lagerstroemia ovalifolia* decreased in a manner dependent on the concentration of the extract.

Experimental Example 3

Inhibitory Effects of *Lagerstroemia ovalifolia* Extract on the Expression of iNOS Gene and Protein 3-1: Experiment on Inhibition of Expression of iNOS Gene (RT-PCR)

$1\times10^6$ Raw264.7 cells were dispensed into a 100 mm Petri dish and treated with various concentrations of the methanol extract of *Lagerstroemia ovalifolia*. Then, the cells were treated with LPS to induce inflammation and were cultured for 24 hours. Then, the medium was removed, and the cells were detached from the culture dish and homogenized using RNA extraction solution (Invitrogen, Calif., USA). After 5 minutes, the cells were collected and transferred into a centrifuge tube, and 200 μl of chloroform was added thereto and completely mixed for 15 seconds. The cell solution was allowed to stand for 3 minutes, and then centrifuged at 14000 rpm for 15 minutes. The RNA-containing supernatant was transferred into a fresh tube and mixed with 500 μl of isopropyl alcohol. After 10 minutes, the solution was centrifuged, and the supernatant was discarded. 1 ml of 75% ethanol was added to the precipitate, which was then centrifuged at 10000 rpm for 5 minutes. Then, the supernatant was removed, and the precipitated RNA was dried at room temperature for 20 minutes. The dried RNA was suspended in distilled water treated with DEPC (diethyl pyrocarbonate, Sigma). After quantification, the RNA was synthesized into cDNA using RT-PreMix (AccuPower RT PreMix, Bioneer). The synthesized cDNA as a template was mixed with iNOS primers, and then subjected to PCR using PCR premix (AccuPower PCR PreMix, Bioneer) to determine the expression level of the RNA.

As a result, as can be seen in FIG. 3b), treatment with LPS increased the expression of iNOS, but the expression level of the iNOS gene in the group treated with the methanol extract of *Lagerstroemia ovalifolia* in a manner dependent on the concentration of the extract.

3-2: Experiment on Inhibition of Expression of iNOS Protein (Western Blotting)

$1 \times 10^6$ Raw264.7 cells were dispensed into a 100 mm Petri dish and treated with various concentrations of the methanol extract of *Lagerstroemia ovalifolia*. Then, the cells were treated with LPS to induce inflammation and were cultured for 24 hours. Then, the medium was removed, and the cells were detached from the culture dish and homogenized using a protein lysis solution (CelLytic™-MT Tissue Lysis Reagent, Sigma) comprising a protease inhibitor cocktail (Roche). The resulting solution was centrifuged at 14000 rpm for 20 minutes, and the supernatant was separated from the insoluble aggregate. The concentration of protein in the separated supernatant was measured using a Bio-Rad protein assay kit (Bio-Rad). Also, the supernatant was mixed with 5×SDS (0.156M Tris-HCl, pH 6.8, 2.5% SDS, 37.5% glycerol, 37.5 mM DTT) at a ratio of 1:4 and boiled at 100° C. for 10 minutes. 40 µg of protein from the boiled sample was loaded onto 4-12% SDS-PAGE and electrophoresed at 125 V for 2 hours to separate it according to molecular weight. The separated protein was electrophoresed at 50 mA per gel for 1 hour and transferred to a PVDF membrane. The protein-free portion of the membrane was blocked with defatted milk, and then treated sequentially with primary antibody [anti-iNOS antibody (1:1000, Santa Cruz Biotechnology)] and secondary antibody (anti-rabbit-IgG-HRP, Amersham Biosciences). Next, the membrane was visualized using an ECL detection kit (Amersham Biosciences, UK) and exposed to X-ray films.

As a result, as can be seen in FIG. 3c), with the macrophages were treated with the methanol extract of *Lagerstroemia ovalifolia*, the LPS-induced expression of iNOS protein in the cells decreased in a manner dependent on the concentration of the extract.

Experimental Example 4

Inhibitory Effect of *Lagerstroemia ovalifolia* Extract on Production of Prostaglandin In order to examine the inhibitory effect of the *Lagerstroemia ovalifolia* extract on the production of prostaglandin $E_2$, the following experiment was performed. Specifically, according to the method described in Experimental Example 3-1, the culture supernatant of the Raw264.7 cells treated with the methanol extract of *Lagerstroemia ovalifolia* and LPS was collected, and the production of prostaglandin $E_2$ in the supernatant was measured using a PGE2 assay kit (R&D Systems, Minneapolis).

As a result, as can be seen in FIG. 4a), treatment with the methanol extract of *Lagerstroemia ovalifolia* reduced the production of prostaglandin $E_2$ in a concentration-dependent manner.

Experimental Example 5

Inhibitory Effects of *Lagerstroemia ovalifolia* Extract on Expression of COX-2 Gene and Protein

5-1: Experiment on Inhibition of Expression of COX-2 Gene (RT-PCR)

According to the method described in Experimental Example 3-1, cells were treated with various concentrations of the *Lagerstroemia ovalifolia* extract and treated with LPS to induce inflamuation. After culture of the cells for 24 hours, RNA was extracted, quantified, and then synthesized into cDNA using RT-PreMix (AccuPower RT PreMix, Bioneer). The synthesized cDNA as a template was mixed with COX-2 primers and subjected to PCR using PCR Premix (AccuPower PCR PreMix, Bioneer) to determine the expression level of the RNA.

As a result, as can be seen in FIG. 4b), treatment with LPS increased the expression of iNOS, but the mRNA expression of COX-2 in the groups treated with the *Lagerstroemia ovalifolia* extract significantly decreased in a manner dependent on the concentration of the extract.

5-2: Experiment on Inhibition of Expression of COX-2 Protein (Western Blotting)

According to the same manner as described in Experimental Example 3-2, protein was separated, and then 40 µg of the protein was electrophoresed on 4-12% SDS-PAGE gel and transferred to a PVDF membrane. The protein-free portion of the membrane was blocked with defatted milk, and then treated sequentially with primary antibody [anti-COX-2 antibody (1:1000, Santa Cruz Biotechnology)] and secondary antibody (anti-goat-IgG-HRP; Amersham Biosciences). Then, the membrane was visualized using an ECL detection kit (Amersham Biosciences, UK) and exposed to an X-ray film.

As a result, as can be seen in FIG. 4c), when the macrophages were treated with the *Lagerstroemia ovalifolia* extract, the LPS-induced expression of COX-2 protein decreased in a manner dependent on the concentration of the extract.

Experimental Example 6

Inhibitory Effects of *Lagerstroemia ovalifolia* Extract Against Production of Cytokines In order to examine the inhibitory effects of the *Lagerstroemia ovalifolia* extract against the production of cytokines in Raw264.7 cells treated with LPS, the LPS-induced production of IL-6 and IL-1 beta was measured using a mouse IL-6 enzyme immunometric assay kit and a mouse IL-1-beta enzyme immunometric assay kit (BD Bioscience). Specifically, 100 µl of the cell culture treated according to the same method as described in Experimental Example 2 was added to each well of a 96-well plate coated with mouse immunoglobulin and was stirred for 2 hours. Then, the plate was washed four timed with a washing solution, and 100 µl of primary antibody was added to each well and allowed to react for 2 hours. Then, secondary antibody was added to each well and allowed to react for 30 minutes. After the plate was washed again, and a substrate was added to each well and allowed to react for 30 minutes, and then the absorbance at 450 nm was measured using a microplate reader.

As a result, as can be seen in FIG. 5, the levels of IL-6 and IL-1-beta in the group treated with LPS increased, but decreased after treatment with the methanol extract of *Lagerstroemia ovalifolia* extract in a manner dependent on the concentration of the extract.

Example 7

Experimental Animals and Induction of Bronchial Asthma by Ovalbumin

In this experiment, 6 week-old Balb/c female mice (average weight: about 20 g) were used as experimental animals. The animals were acclimated for 1 week, and animals showing no abnormality in the basic physical examination were selected. Specifically, the selected experimental animals were sensitized by intraperitoneally injecting 200 µl of a suspension of 2 mg of aluminum hydroxide (A8222, Sigma, St. Louis, Mo.) and 20 µg of ovalbumin (A5503, Sigma, St. Louis, Mo.) in phosphate buffered saline (pH 7.4) at 2 week-intervals. From 28 days to 30 days from the first intraperitoneal injection of ovalbumin, 1% ovalbumin was inhaled by an ultrasonic atomizer for 30 minutes. At 24 hours after final injection of the antigen, the airway hypersensitivity of the mice was measured, and at 48 hours, a lethal dose of pentobarbital (Entobar®; Hanlim Pharm Co., Ltd.) was administered, and then the mice were weighed and subjected to tracheostomy. Then, the mice were subjected to bronchoalveolar lavage with a total of 1.2 ml of physiological saline, after which the sample was collected. The animals used in this experiment were grouped into the following groups: a normal control (NC) group administered with no ovalbumin; an asthma-induced group (OVA) administered with ovalbumin to induce bronchial asthma; a comparative group administered orally with montelukast (30 ml/kg, PO) at 1 hour before inhalation of ovalbumin; and a test group (LO-T or LO-EA) administered orally with the methanol extract of *Lagerstroemia ovalifolia* or the ethyl acetate fraction of the extract at 1 hour before inhalation of ovalbumin. Each of the groups consisted of 7 mice.

Experimental Example 8

Measurement of Airway Hypersensitivity

Airway hypersensitivity caused by the development of asthma was evaluated by measuring airway resistance by one chamber plethysmography (All Medicus, Seoul), and the degree of airway resistance was evaluated by measuring enhanced pause (Penh) that indicates mathematically calculated airway obstruction. To measure Penh, the baseline value was measured under a normal respiratory condition, and then PBS was inhaled using an ultrasonic atomizer for 3 min, and Penh values were measured over 3 min. Then, gradually increasing concentrations (12, 25 and 50 ml/kg) of histamine methacholine (A2251, Sigma, St. Louis, Mo.) was inhaled, followed by measurement of Penh. Penh value was calculated according to the following equation 1, and the resulting Penh value was expressed as a percent increase in Penh after inhalation of each concentration of methacholine. The baseline Penh (saline challenge) was expressed as 100%.

$$\text{Penh} = [\text{Te}/(\text{RT}-1)] \times (\text{PEF}/\text{PIF}) \qquad \text{Equation 3}$$

Te: expiratory time (sec), the time from inspiration to the next inspiration;

RT: relaxation time, the elapsed time between the beginning of the expiration and the moment when the remaining 30% of the tidal volume has been reached during expiration;

PEF: Peak expiration flow;

PIF: Peak inspiration flow.

Figure 6:
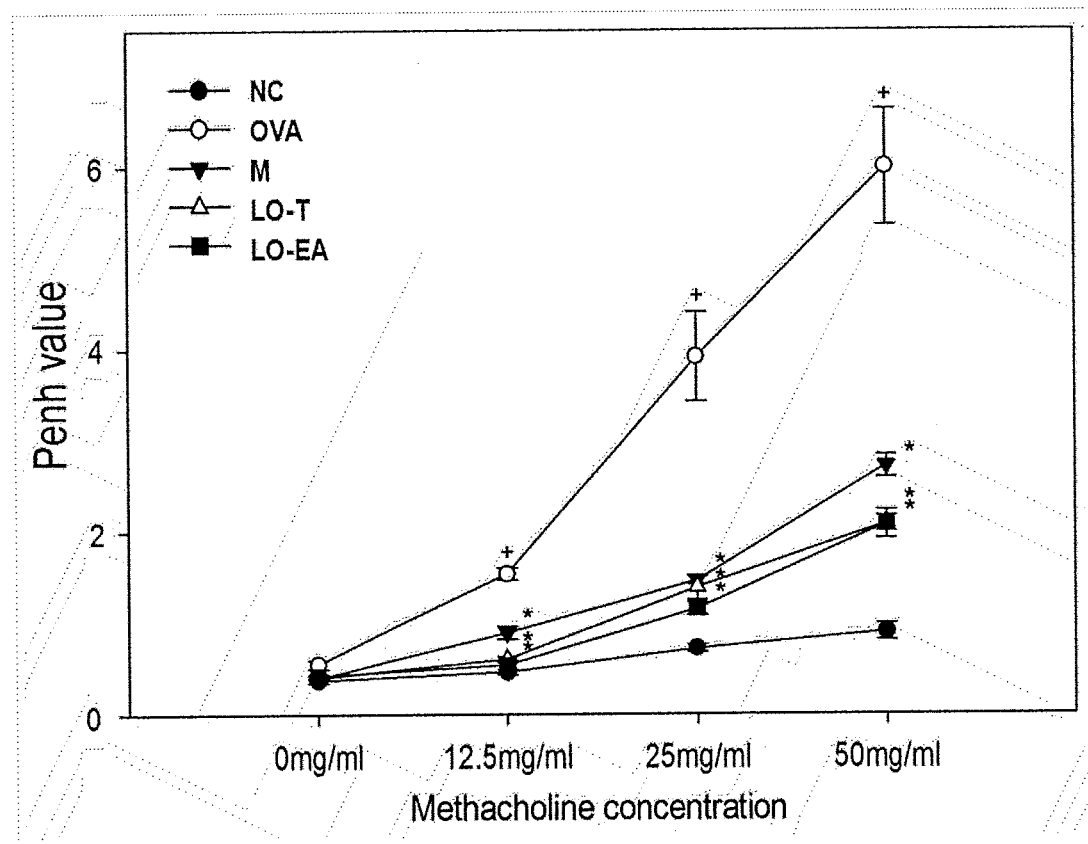
FIG. 6 shows effects on respiratory rate after airway sensitization. NC: negative control group whose airway was not sensitized; OVA: positive control group whose airway was sensitized with ovalbumin; M: comparative control group administered with 30 mg/kg of Montelukast; LO-T: group administered with 30 mg/kg of a methanol extract of *Lagerstroemia ovalifolia*; LO-EA: group administered with 30 mg/kg of an ethyl acetate fraction of *Lagerstroemia ovalifolia*.

As a result, as can be seen in FIG. 6, the negative control (NC) group showed a slow increase in Penh value as the concentration of methacholine increased, but the group with ovalbumin-induced asthma (OVA) showed an abrupt increase in Penh value.

However, the Penh value in the comparative group (M) and the group (LO-T or LO-EA) administered with the methanol extract of *Lagerstroemia ovalifolia* or a fraction thereof significantly decreased compared to that in the asthma-induced group (OVA) regardless of the concentration of methacholine and decreased in a manner dependent on the concentration of the extract or fraction. In addition, this difference was more evident when a high concentration of methacholine was inhaled compared to when a low concentration of methacholine was inhaled.

Experimental Example 9

Analysis of Inflammatory Cells in Bronchoalveolar Lavage Fluid

Bronchoalveolar lavage fluid of each Mouse was stained with trypan blue immediately after collection. The total number of cells excluding dead cells in the bronchoalveolar lavage fluid was calculated using a hemocytometer. Then, Diff-Quick staining (Sysmex, Swizerland) was performed after smear preparation with Cytospin II, and eosinophils and other inflammatory cells were differentially counted.

Figure 7:
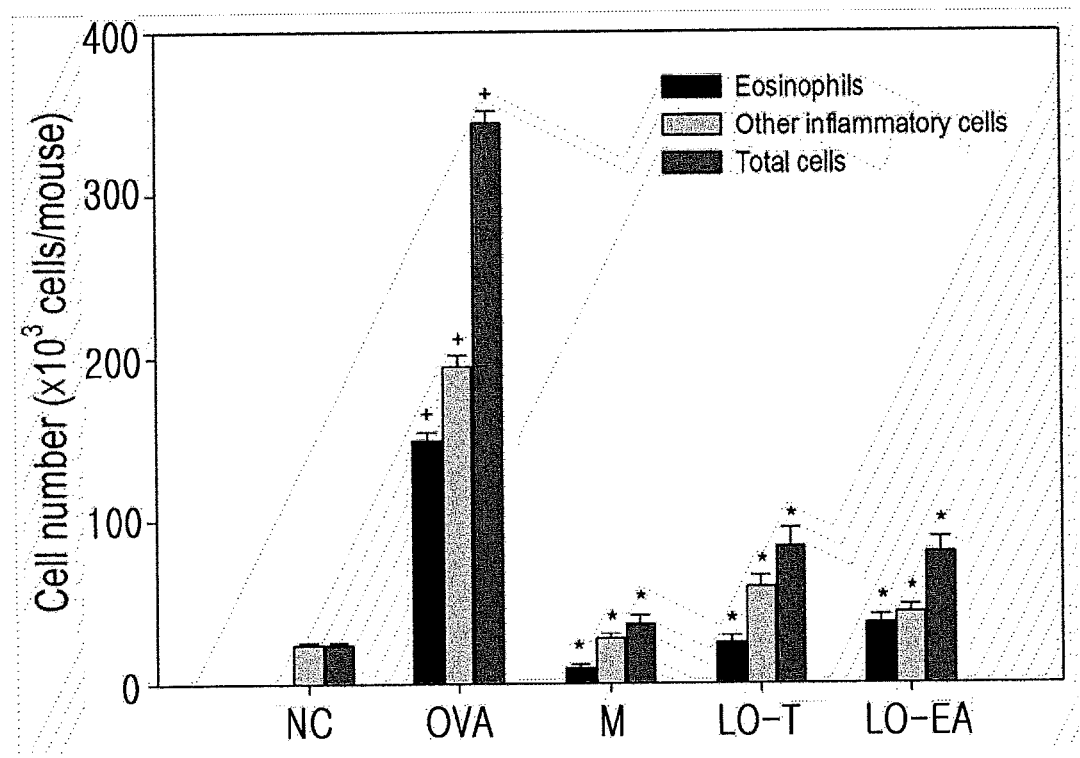
FIG. 7 shows the effects of a methanol extract and ethyl acetate fraction of *Lagerstroemia ovalifolia* on the numbers of total cells and eosinophils in bronchoalveolar lavage fluid after airway sensitization. NC: negative control group whose airway was not sensitized; OVA: positive control group whose airway was sensitized with ovalbumin; M: comparative control group administered with 30 mg/kg of Montelukast; LO-T: group administered with 30 mg/kg of a methanol extract of *Lagerstroemia ovalifolia*; LO-EA: group administered with 30 mg/kg of an ethyl acetate fraction of *Lagerstroemia ovalifolia*.

As a result, as can be seen in FIG. 7, the total number of inflammatory cells rapidly increased in the asthma-induced group (OVA) compared to the normal control group (NC), rapidly decreased in the comparative group (M), and significantly decreased in all the groups (LO-T and LO-EA) administered with the methanol extract of *Lagerstroemia ovalifolia* and a fraction thereof.

Experimental Example 10

Measurement of Cytokines in Bronchoalveolar Lavage Fluid

In order to measure the levels of cytokines in bronchoalveolar lavage fluid of each mouse, which increase upon induction of asthma, a sandwich-type enzyme-linked immunosorbent assay (ELISA) was used. To measure Th2 type-cytokines, IL-4, IL-5 and IL-13 ELISA kits were used, and to measure inflammation-related cytokines, IL-6, IL-1beta and TNF-alpha ELISA kits were used.

Each of the bronchoalveolar lavage fluids was added to a 96-well plate coated with cytokine antibody, and an antigen-antibody reaction in the plate was induced for 2 hours. The experiment was performed according to the instructions of the kit.

Figure 8:
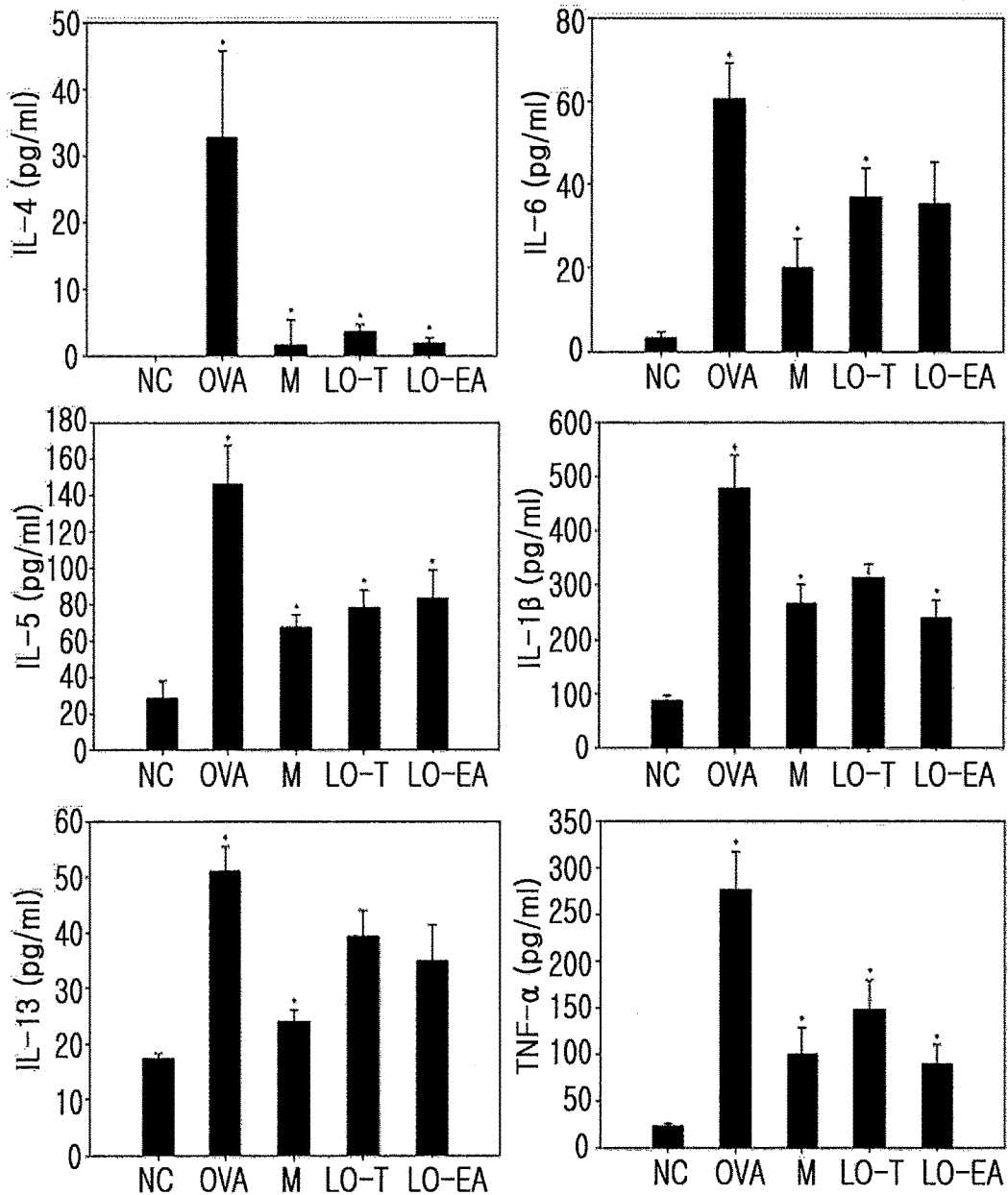
FIG. 8 shows the results of measuring the cytokine content of bronchoalveolar lavage fluid after airway sensitization. NC: negative control group whose airway was not sensitized; OVA: positive control group whose airway was sensitized with ovalbumin; M: comparative control group administered with 30 mg/kg of Montelukast; LO-T: group administered with 30 mg/kg of a methanol extract of *Lagerstroemia ovalifolia*; LO-EA: group administered with 30 mg/kg of an ethyl acetate fraction of *Lagerstroemia ovalifolia*.

As a result, as can be seen in FIG. 8, the production of cytokines rapidly increased in the asthma-induced group (OVA) compared to the normal control group (NC), but significantly decreased in all the comparative group and the groups (LO-T and LO-EA) administered with the methanol extract of *Lagerstroemia ovalifolia* and a fraction thereof.

Experimental Example 11

Measurement of Serum IgE

To measure the levels of total IgE and ovalbumin-specific IgE in serum, an enzyme-linked immunosorbent assay (ELISA) was used. Specifically, IgE or OVA was dissolved in 0.1 M $NaHCO_3$ buffer (pH 8.3) at a concentration of 20 μg/ml, and a 96-well flat bottom ELISA plate was coated overnight with the solution at 4° C., and then treated with 1% bovine serum albumin-comprising PBS to inhibit non-specific reactions. The serum sample was diluted at 1:400 and allowed to react at room temperature for 2 hours. After sufficiently washing the plate, anti-mouse IgE monoclonal antibody was 300-fold diluted and allowed to react with the sample for 2 hours, and then HRP-conjugated goat anti-rat IgG polyclonal antibody was 4000-fold diluted and allowed to react with the sample at room temperature for 1 hour, followed by washing. 3,3',5,5'-tetramethylbezidine substrate for color development was added to the plate, and then the absorbance at 450 nm was measured.

Figure 9:
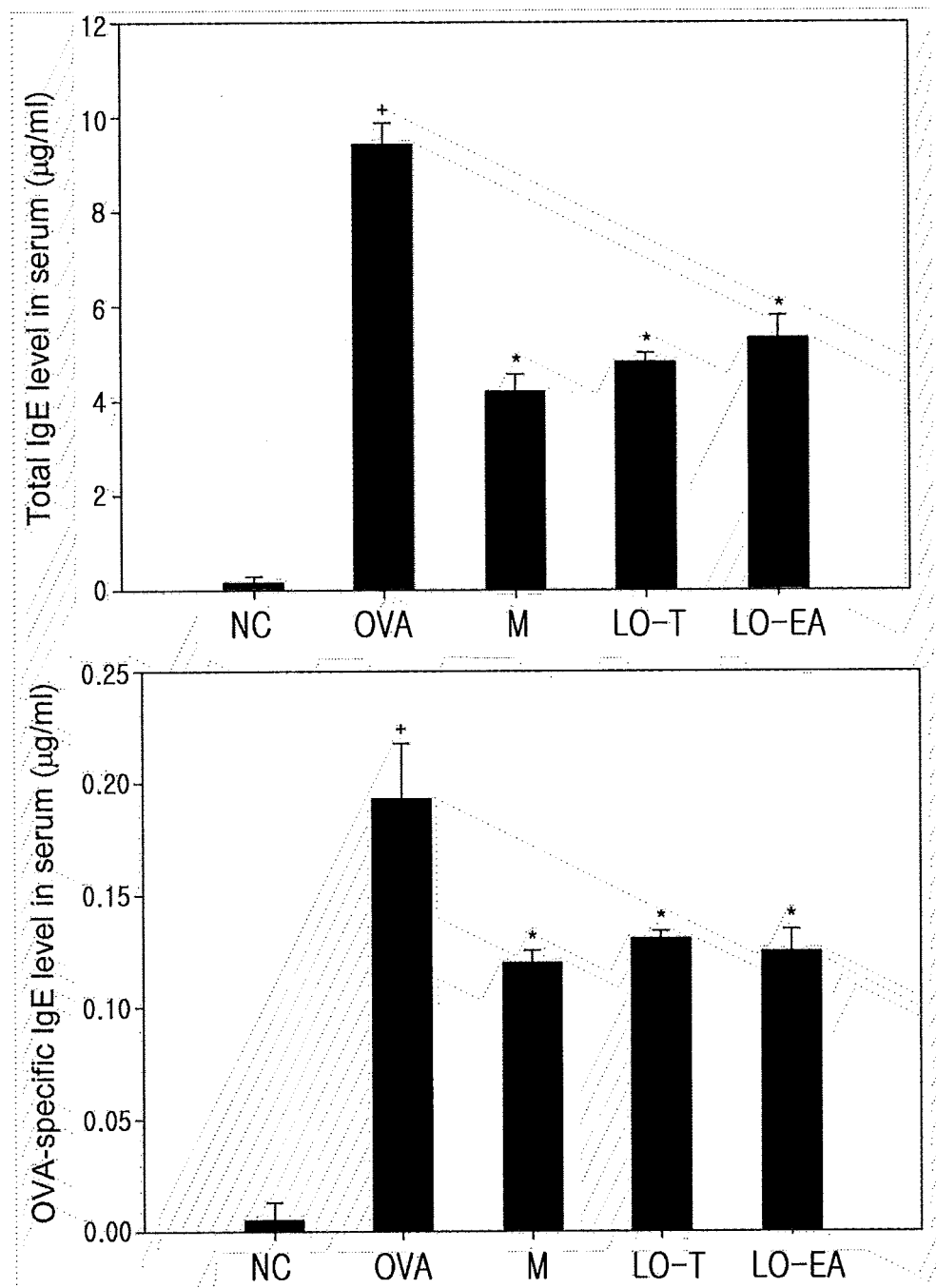
FIG. 9 shows the results of measuring the immunoglobulin content of blood after airway sensitization. NC: negative control group whose airway was not sensitized; OVA: positive control group whose airway was sensitized with ovalbumin; M: comparative control group administered with 30 mg/kg of Montelukast; LO-T: group administered with 30 mg/kg of a methanol extract of *Lagerstroemia ovalifolia*; LO-EA: group administered with 30 mg/kg of an ethyl acetate fraction of *Lagerstroemia ovalifolia*.

As a result, as can be seen in FIG. 9, the results of measuring the concentration of IgE antibody in serum indicated that the concentration of IgE antibody in serum rapidly increased in the ovalbumin-induced asthma group (OVA) compared to the normal control group. Also, it was shown that the concentrations of IgE in the groups (LO-T and LO-EA) administered with the methanol extract of *Lagerstroemia ovalifolia* and a fraction thereof significantly decreased compared to that in the asthma-induced group (OVA) showing increased IgE concentration. In addition, the concentration of ovalbumin-specific IgE antibody in serum was also significantly higher in the groups (LO-T and LO-EA) administered with the methanol extract of *Lagerstroemia ovalifolia* and a fraction thereof than in the asthma-induced group (OVA).

Example 12

Histopathological Examination

In order to evaluate the degree of inflammation in lung tissue, extracted lung tissue was generally fixed with formalin, embedded in paraffin and sectioned to a thickness of 4 μm. The tissue section was stained with hematoxylin and eosin Y (ThermoShandon, Pittsburgh, Pa.), and then mounted with Dako-mounting medium (Dakocytomation, Denmark). After staining and mounting, the slide was observed with an optical microscope. After H & E staining, the inflammation scores of five random sites per tissue section of each individual were measured and averaged. The inflammation scores were rated on the following scale: 1: intermittent observation of inflammatory cells; 2: observation of 1-3 thin inflammatory cell layers around most bronchi; 3: observation of 2-5 inflammatory cell layers around most bronchi; and 4: observation of 5 or more thick inflammatory cell layers around most bronchi. The ratio of goblet cells identified by PAS (periodic acid Schiff) staining in bronchial epithelial cells was measured to determine the degree of proliferation of goblet cells. All measurements were performed using a computerized image analyzer program.

Figure 10:
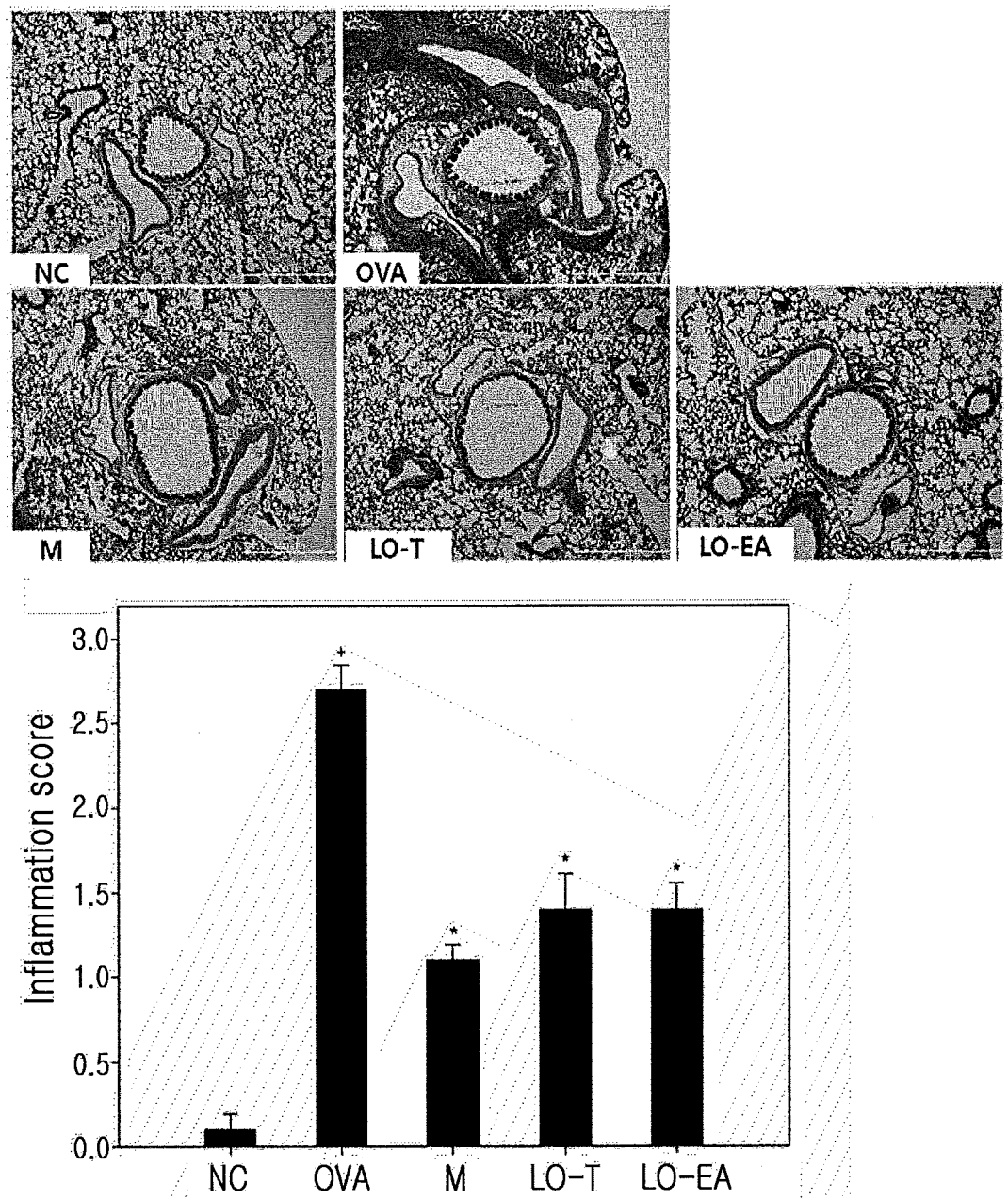
FIG. 10 shows the results of H & E staining performed to examine the degree of infiltration of inflammatory cells into airway mucus after airway sensitization. NC: negative control group whose airway was not sensitized; OVA: positive control group whose airway was sensitized with ovalbumin; M: comparative control group administered with 30 mg/kg of Montelukast; LO-T: group administered with 30 mg/kg of a methanol extract of *Lagerstroemia ovalifolia*; LO-EA: group administered with 30 mg/kg of an ethyl acetate fraction of *Lagerstroemia ovalifolia*.

As can be seen in FIG. 10 showing the results of H & E staining, epithelial cells were damaged in the ovalbumin-induced asthma group (OVA) compared to the normal control group (NC) whose airway was not sensitized, and many inflammatory cells including eosinophils were infiltrated around bronchioles. However, in the comparative group (M) and the groups (LO-T and LO-EA) administered with the methanol extract of *Lagerstroemia ovalifolia* and a fraction thereof, inflammatory cells including eosinophils significantly decreased, and little or no damage to epithelial cells appeared. Such results are consistent with the results of FIG. 7 which shows decreases in the numbers of total inflammatory cells and eosinophils.

Figure 11:
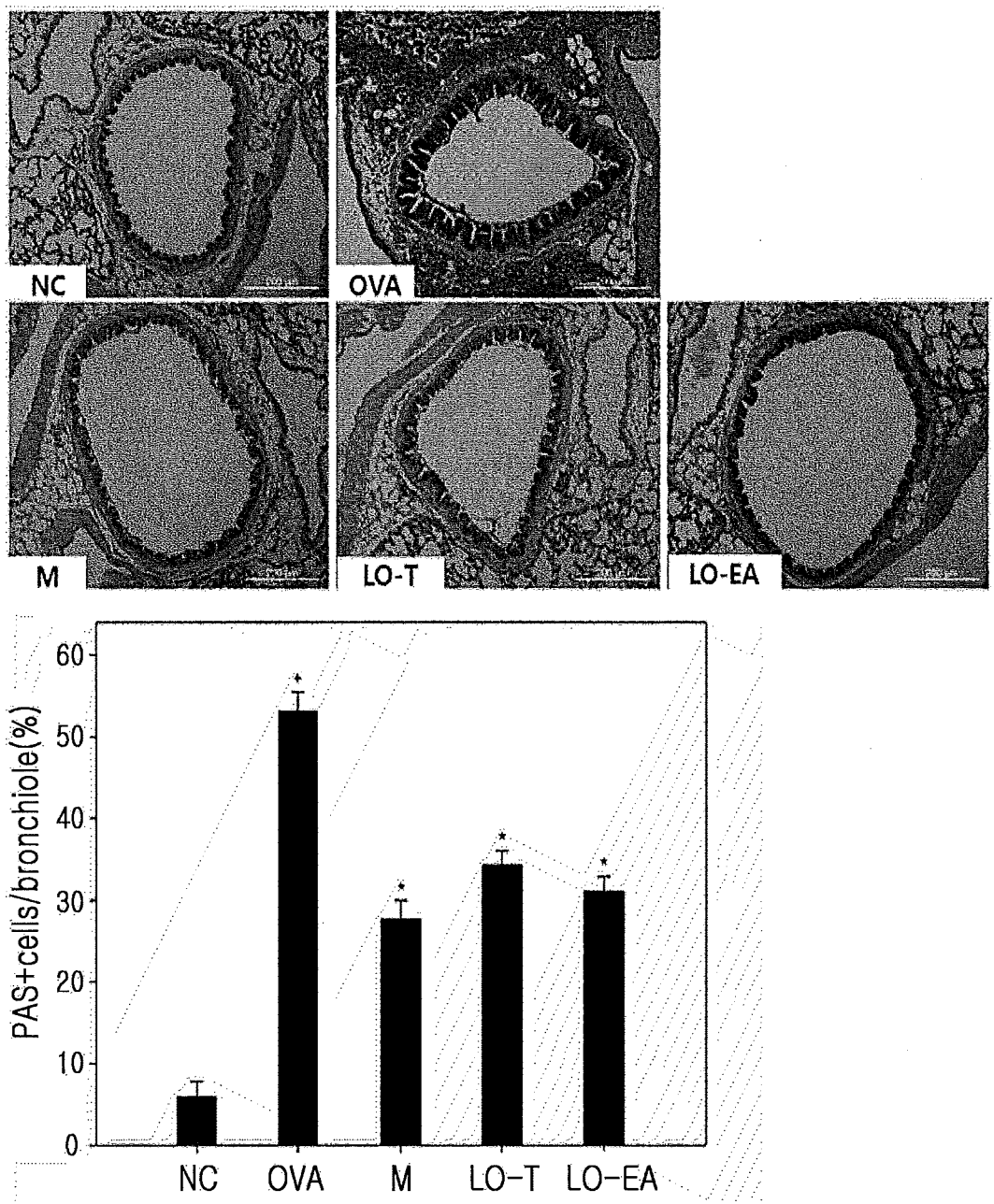
FIG. 11 shows the results of PAS staining performed to examine the ratio of globlet cells in mouse epithelial cells after airway sensitization. NC: negative control group whose airway was not sensitized; OVA: positive control group whose airway was sensitized with ovalbumin; M: comparative control group administered with 30 mg/kg of Montelukast; LO-T: group administered with 30 mg/kg a methanol extract of *Lagerstroemia ovalifolia*; LO-EA: group administered with 30 mg/kg of an ethyl acetate fraction of *Lagerstroemia ovalifolia*.

Meanwhile, as shown in FIG. 11 showing the results of PAS staining, the ratio of globlet cells in epithelial cells of bronchioles was very low in the normal control group whose airway was not sensitized, but it significantly increased in the ovalbumin-induced asthma group (OVA). In addition, it was shown that, in the groups (LO-T and LO-EA) administered with the methanol extract of *Lagerstroemia ovalifolia* and a fraction thereof, the number of globlet cells significantly decreased, and thus the secretion of mucus was also inhibited.

Experimental Example 13

Statistical Analysis

Mean values and standard deviations (mean S.E.) according to various variables were calculated. The comparison between groups was performed by Mann-whitney U test using SPSS 10.0. $p<0.05$ was considered statistically significantly different.

The invention claimed is:

1. A method for treating inflammatory disease or asthma comprising administering to a subject in need thereof a pharmaceutical composition comprising a *Lagerstroemia ovalifolia* extract, wherein the extract is prepared by extraction with water, a $C_1$-$C_4$ alcohol, or a mixture thereof.

2. The method according to claim 1, wherein the extract is prepared by extraction with methanol.

3. The method according to claim 1, wherein the inflammatory disease is any one or more selected from the group consisting of systemic lupus erythematosus, scleroderma, ulcerative colitis, Crohn's disease, atopic dermatitis, psoriasis, anaphylaxis, dermatitis, diabetic retinopathy, retinitis, macular degeneration, uveitis, conjunctivitis, arthritis, rheumatoid arthritis, ankylosing spondylitis, osteoarthritis, osteoporosis, allergy, diabetes, diabetic nephropathy, nephritis, Sjögren's syndrome, autoimmune pancreatitis, periodontal disease, asthma, graft-versus-host disease, chronic pelvic inflammatory disease, endometritis, nasitis, tonsillitis, otitis media, pharyngitis, cystitis, and chronic prostatitis.

4. The method according to claim 1, wherein the extract exhibits the following activity:
    (a) inhibitory activity against the production of nitric oxide (NO) in macrophages;
    (b) inhibitory activity against the expression of inducible nitric oxide synthase (iNOS) in macrophages;
    (c) inhibitory activity against the production of prostaglandin $E_2$ ($PGE_2$) in macrophages;
    (d) inhibitory activity against the expression of cyclooxygenase-2 (COX-2);
    (e) inhibitory activity against the production of IL-6; or
    (f) inhibitory activity against the production of IL-1β.

5. A method for ameliorating inflammatory disease or asthma comprising administering to a subject in need thereof a health functional food comprising a *Lagerstroemia ovalifolia* extract, wherein the extract is prepared by extraction with water, a $C_1$-$C_4$ alcohol, or a mixture thereof.

6. A method for ameliorating inflammatory disease or asthma comprising administering to a subject in need thereof a feed additive comprising a *Lagerstroemia ovalifolia* extract, wherein the extract is prepared by extraction with water, a $C_1$-$C_4$ alcohol, or a mixture thereof.

* * * * *